US011490930B2

(12) United States Patent
Ritchey et al.

(10) Patent No.: US 11,490,930 B2
(45) Date of Patent: Nov. 8, 2022

(54) INTERNAL PELVIC FIXATOR

(71) Applicant: Smith & Nephew, Inc., Memphis, TN (US)

(72) Inventors: Nick Ritchey, Collierville, TN (US); Joe Ferguson, Ponte Vedra Beach, FL (US); James Brownhill, Warsaw, IN (US)

(73) Assignee: Smith & Nephew, Inc., Memphis, TN (US)

(*) Notice: Subject to any disclaimer, the term of this patent is extended or adjusted under 35 U.S.C. 154(b) by 337 days.

(21) Appl. No.: 16/747,288

(22) Filed: Jan. 20, 2020

(65) Prior Publication Data

US 2020/0146720 A1 May 14, 2020

Related U.S. Application Data

(62) Division of application No. 15/736,102, filed as application No. PCT/US2016/038745 on Jun. 22, 2016, now Pat. No. 10,575,874.

(Continued)

(51) Int. Cl.
*A61B 17/04* (2006.01)
*A61B 17/86* (2006.01)
(Continued)

(52) U.S. Cl.
CPC .......... *A61B 17/68* (2013.01); *A61B 17/6433* (2013.01); *A61B 17/66* (2013.01);
(Continued)

(58) Field of Classification Search
CPC combination set(s) only.
See application file for complete search history.

(56) References Cited

U.S. PATENT DOCUMENTS 5,601,550 A * 2/1997 Esser ................ A61B 17/6433
606/54

FOREIGN PATENT DOCUMENTS

| CH | 685532 A5 | 8/1995 |
|---|---|---|
| WO | 2011121512 A2 | 12/2011 |
| WO | 2012019835 A2 | 2/2012 |

OTHER PUBLICATIONS

First Office Action for Chinese Patent Application No. 201680048613.X, dated Dec. 19, 2019.

(Continued)

*Primary Examiner* — Sameh R Boles
(74) *Attorney, Agent, or Firm* — KDB Firm PLLC

(57) ABSTRACT

A system and method for internal pelvic fixation. Guide wires can be inserted through guides and opposing sides of a pelvic bone, and can indicate a depth for driving bone screws into the pelvic bone. Offset rod tools positioned about each guide can assist in determining an offset distance between an implant rod and the pelvic bone. A template rod may be coupled to the offset rod tools and used to select a length for the implant rod. Clamps can be coupled to the bone screws, the clamps having multiple axes of rotation, the angular positions of the clamps being secured by the tightening of a single nut of each clamp. Joysticks used to tighten the nuts can be coupled to a reduction holder mechanism that can decrease at least an axial distance between the clamps, and thus pelvic bones, before locking of the clamps via tightening of the nuts.

11 Claims, 22 Drawing Sheets

Related U.S. Application Data

(60) Provisional application No. 62/182,924, filed on Jun. 22, 2015.

(51) Int. Cl.

| | | |
|---|---|---|
| *A61F 2/08* | (2006.01) | |
| *A61B 17/68* | (2006.01) | |
| *F16B 2/12* | (2006.01) | |
| *F16B 1/00* | (2006.01) | |
| *A61B 17/64* | (2006.01) | |
| *A61B 17/66* | (2006.01) | |
| *A61B 17/88* | (2006.01) | |
| *A61B 90/00* | (2016.01) | |
| *A61B 17/00* | (2006.01) | |

(52) U.S. Cl.
CPC ............ *A61B 17/683* (2013.01); *A61B 17/86* (2013.01); *A61B 17/8863* (2013.01); *A61B 17/8875* (2013.01); *A61B 17/8897* (2013.01); *F16B 1/0071* (2013.01); *F16B 2/12* (2013.01); *A61B 17/6441* (2013.01); *A61B 2017/00367* (2013.01); *A61B 2017/681* (2013.01); *A61B 2090/061* (2016.02)

(56) References Cited

OTHER PUBLICATIONS

Search Report for Chinese Patent Application No. 201680048613.X, dated Dec. 19, 2019.
International Search Report; European Patent Office; International Application No. PCT/US2016/038745; dated Mar. 21, 2017; 7 pages.
Written Opinion of the International Searching Authority; European Patent Office; International Application No. PCT/US2016/038745; dated Mar. 21, 2017; 7 pages.
Muller et al., "The anterior subcutaneous internal fixator (ASIF) for unstable pelvic ring fractures. Clinical and radiological mid-term results", International Orthopaedics (SICOT) (2013) 37:2239-2245.
Scheyerer et al., "Anterior subcutaneous internal fixation for treatment of unstable pelvic fractures", BMC Research Notes 2014, 7:133.

\* cited by examiner

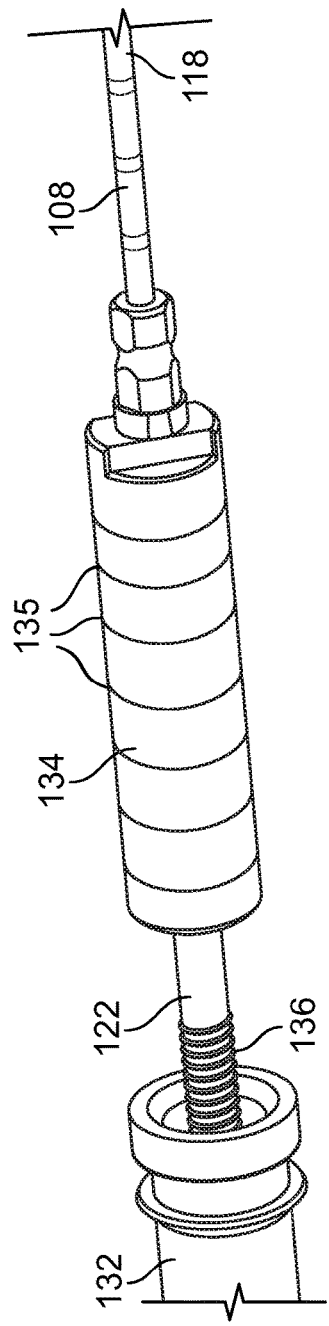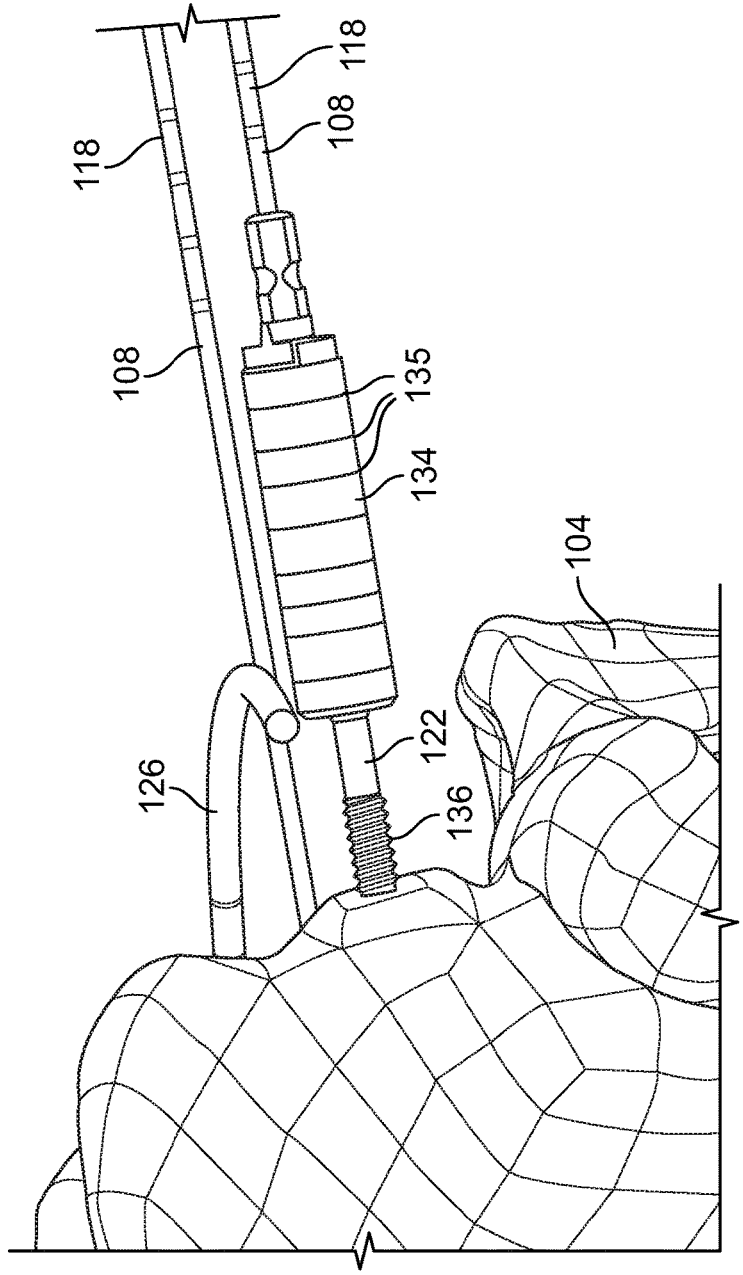
FIG. 5A
FIG. 5B

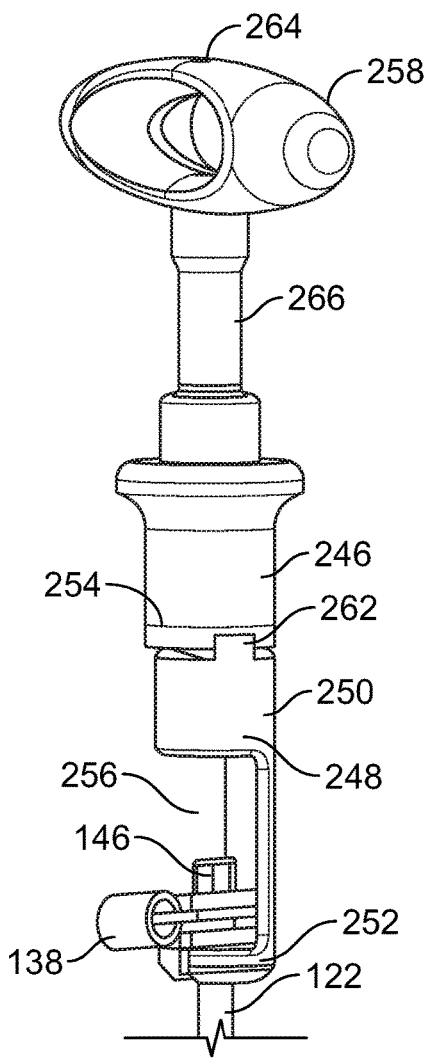
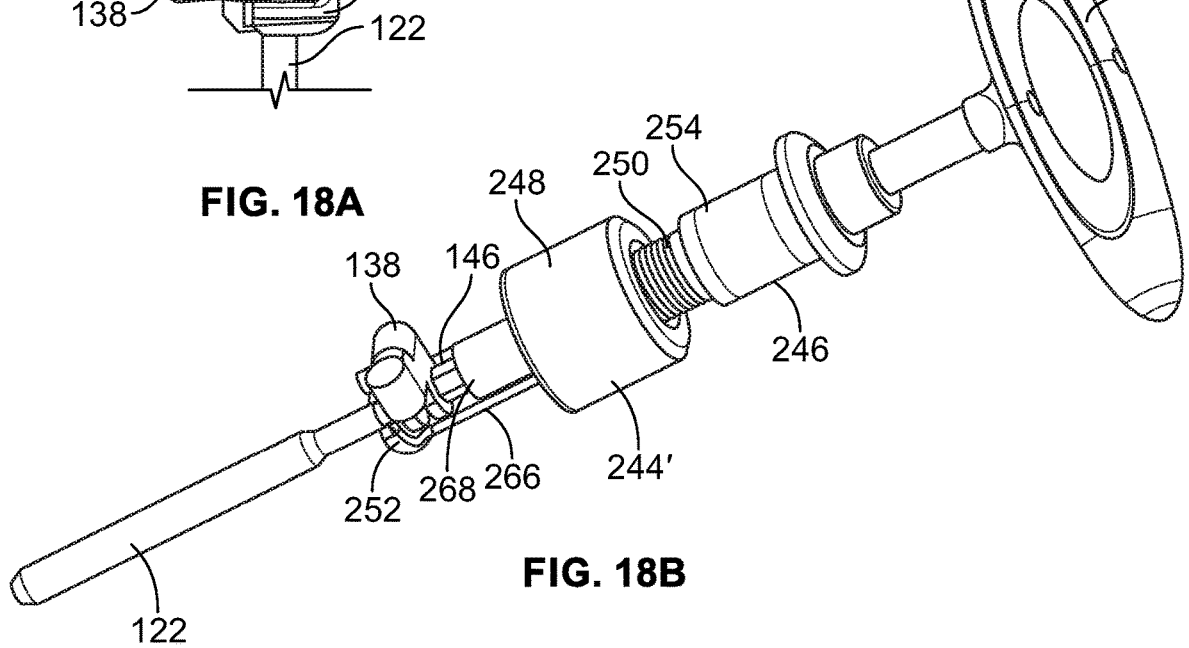
FIG. 18A
FIG. 18B

INTERNAL PELVIC FIXATOR

CROSS-REFERENCE TO RELATED APPLICATIONS

This application is a divisional of U.S. patent application Ser. No. 15/736,102, filed Dec. 13, 2017, which is a U.S. National Phase of International PCT Application No. PCT/US2016/038745, filed Jun. 22, 2016, which claims the benefit of U.S. Provisional Patent Application No. 62/182,924, filed Jun. 22, 2015, the contents of each application hereby incorporated by reference in their entirety.

BACKGROUND

Embodiments of the present application generally relate to an internal fixator that maintains a reduction between two bone structures. More particularly, but not exclusively, embodiments of the present application relate to a system and method for internal pelvic fixation in which an implant rod is coupled to implanted screws for reduction of a fracture in a manner that can accommodate different patient anatomies.

Certain types of implants are utilized to maintain at least a relative position of bone structures during the healing process. Such implants may be temporary, as the implant(s) may be removed from the patient during, or upon completion of, the healing process. For example, certain types of implants may be removed from a patient after the patient's injury has healed and the patient is capable of un-assisted weight bearing. However, the duration of time that an implant may remain in a patient may depend on a variety of different circumstances and/or criteria. For example, in at least certain situations, the removal of an implant used to maintain a relative position or stability of bone structures may be three to six months after implantation.

Additionally, removed implants are typically not intended for subsequent, re-implantation in the patient or another patient. However, there is the potential that, in certain situations, rods and clamps associated with an implant device may be cleaned and re-sterilized if, among other considerations, such components of the implant device have not been modified in any way or previously assembled.

BRIEF SUMMARY

An aspect of an embodiment of the present application is an internal pelvic fixation apparatus for maintaining a reduction of bone structures of a pelvic bone, the internal pelvic fixation apparatus including a first clamp structured to be selectively adjustably rotatable about a first axis, at least a portion of the first clamp also being selectively adjustable about a second axis, the first axis being non-parallel to the second axis. Further, the first clamp has a first clamp bore having a first uncompressed size when the first clamp is in an unlocked state and a first compressed size when the first clamp is in a locked state. The internal pelvic fixation apparatus further includes a second clamp that is structured to be selectively adjustably rotatable about a third axis, at least a portion of the second clamp also being selectively adjustable about a fourth axis, the third axis being non-parallel to the fourth axis. The second clamp has a second clamp bore having a second uncompressed size when the second clamp is in an uncompressed state and a second compressed size when the second clamp is in a locked state. The internal pelvic fixation apparatus also includes an implant rod that is sized to extend to opposing sides of the pelvic bone, the implant rod having a first end and a second end, the first end sized for adjustable insertion though the first clamp bore, the second end sized for adjustable insertion through the second clamp bore. Further, the first compressed size of the first clamp bore and the second compressed size of the second clamp bore can be sized to exert a compression force on the implant rod that prevents movement of the implant rod relative to the first and second clamps.

Another aspect of an embodiment of the present application is an internal pelvic fixation kit that includes at least one template rod that is sized to extend at least between opposing sides of a pelvic bone of a patient, the at least one template rod being manually bendable during implantation to generally conform to the anatomy of the patient. The kit can further include a first clamp and a second clamp, the first and second clamps structured for selective and lockable rotation about one or more axes, the first and second clamps each having a clamping bore, the clamping bore being selectively adjustable between an uncompressed state and a compressed state. Additionally, the kit can further include at least one implant rod, the clamping bore of the first and second clamps sized to receive insertion of an end of the at least one template rod and to exert a clamping force on the at least one template rod when the clamping bore is in the compressed state. The kit can also include at least one guide that is sized to be positioned adjacent to a portion of the pelvic bone, the at least one guide having indicia indicative of an offset position from placement of at least one of the following away from the pelvis bone, the first clamp, the second clamp, the at least one template rod, and the at least one implant rod.

Another aspect of an embodiment of the present application is a method that includes driving a first bone screw about a first depth into a first side of a pelvic bone, and driving a second bone about a second depth into a second side of the pelvic bone. The first bone screw can be coupled to a first clamp, the first clamp can be selectively rotatable about a first axis of the first none screw. Further, at least a portion of the first clamp being rotatable about a first clamp segment axis that is non-parallel to the first axis. A second clamp can be coupled to the second bone screw, the second clamp being selectively rotatable about a second axis of the second bone screw, at least a portion of the second clamp being rotatable about a second clamp segment axis that is non-parallel to the second axis. A first end of the implant rod can be inserted into a first bore of the first clamp, and a second end of the implant rod can be inserted into a second bore of the second clamp. A force can be exerted to decease a distance between at least the first and second clamps from a first distance to a second distance. With the first and second clamps separated by the second distance, the first and second clamps can be tightened, wherein the first and second bores of the tightened first and second clamps exert a compressive force on the implant rod that maintains a relative position of at least the implant rod and the first and second clamps.

BRIEF DESCRIPTION OF THE DRAWINGS

The description herein makes reference to the accompanying figures wherein like reference numerals refer to like parts throughout the several views.

FIG. 5A illustrates a side perspective view of a portion of a depth stop receiving a portion of a screw that is placed over a guide wire and coupled to a screw driver.

FIG. 5B illustrates a side view of a screw that is position about a guide wire being driven the AIIS of a pelvis through use of a screwdriver.

FIG. 18A illustrates a side view of a drive tool structured to remove a screw from a bone of a patient while a clamp remains coupled to the screw.

FIG. 18B illustrates a side view of a drive tool structured to remove a clamp from a screw that is, or has been, implanted into the bone of a patient.

Figure 1A:
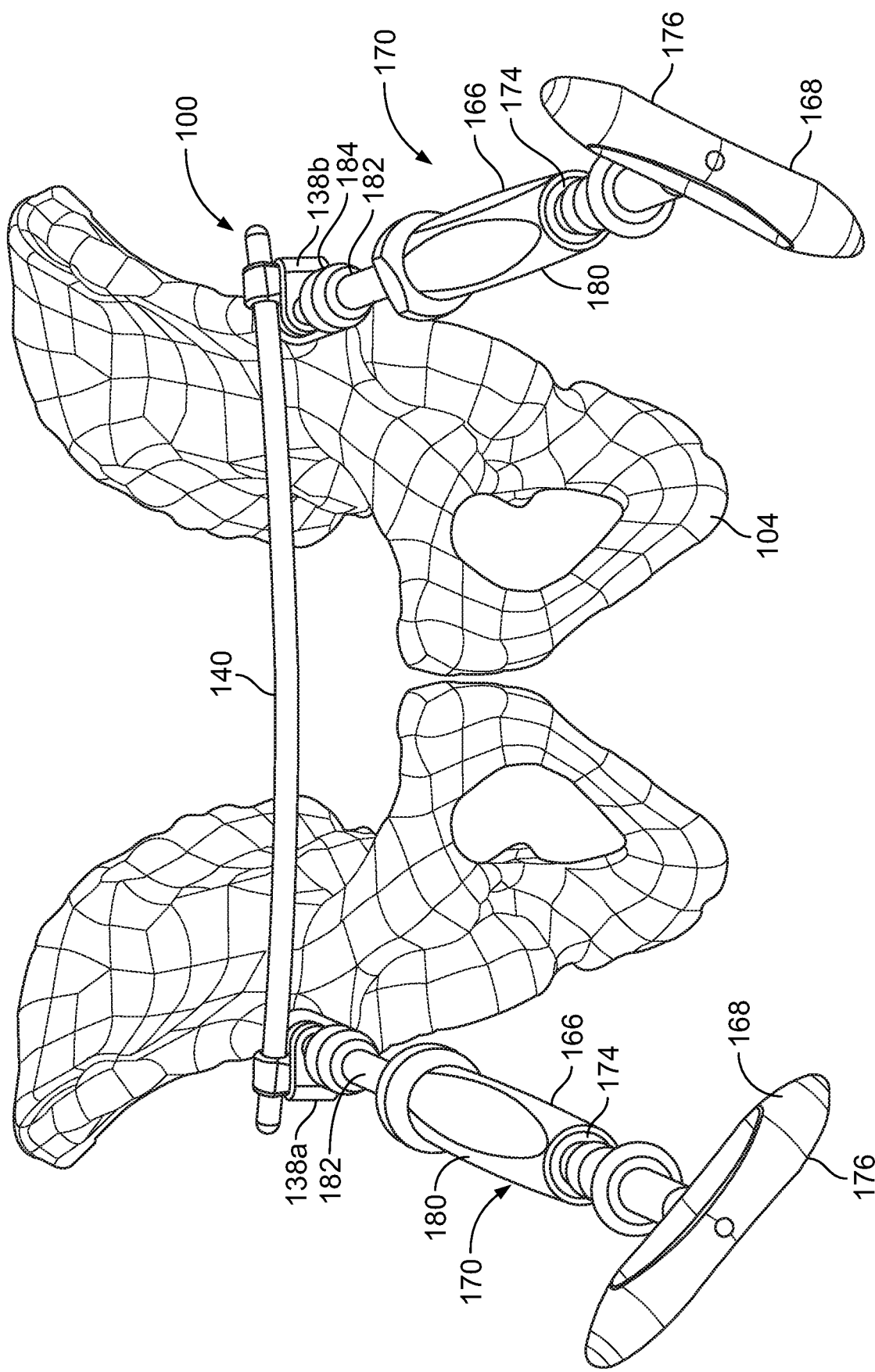
FIG. 1A illustrates a front side view of an implant rod being secured to first and second clamps as a clamping nut on one or more of the screws is/are tightened by operation of the first and/or second joystick(s).

The foregoing summary, as well as the following detailed description of certain embodiments of the present application, will be better understood when read in conjunction with the appended drawings. For the purpose of illustrating the application, there is shown in the drawings, certain embodiments. It should be understood, however, that the present application is not limited to the arrangement and instrumentalities shown in the attached drawings.

DESCRIPTION OF THE ILLUSTRATED EMBODIMENTS

Certain terminology is used in the foregoing description for convenience and is not intended to be limiting. Words such as "upper," "lower," "top," "bottom;" "first," and "second" designate directions is the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more stents, such as "A, B or C," means any individual one of A, B or C, as well as any combination thereof.

Figure 1B:
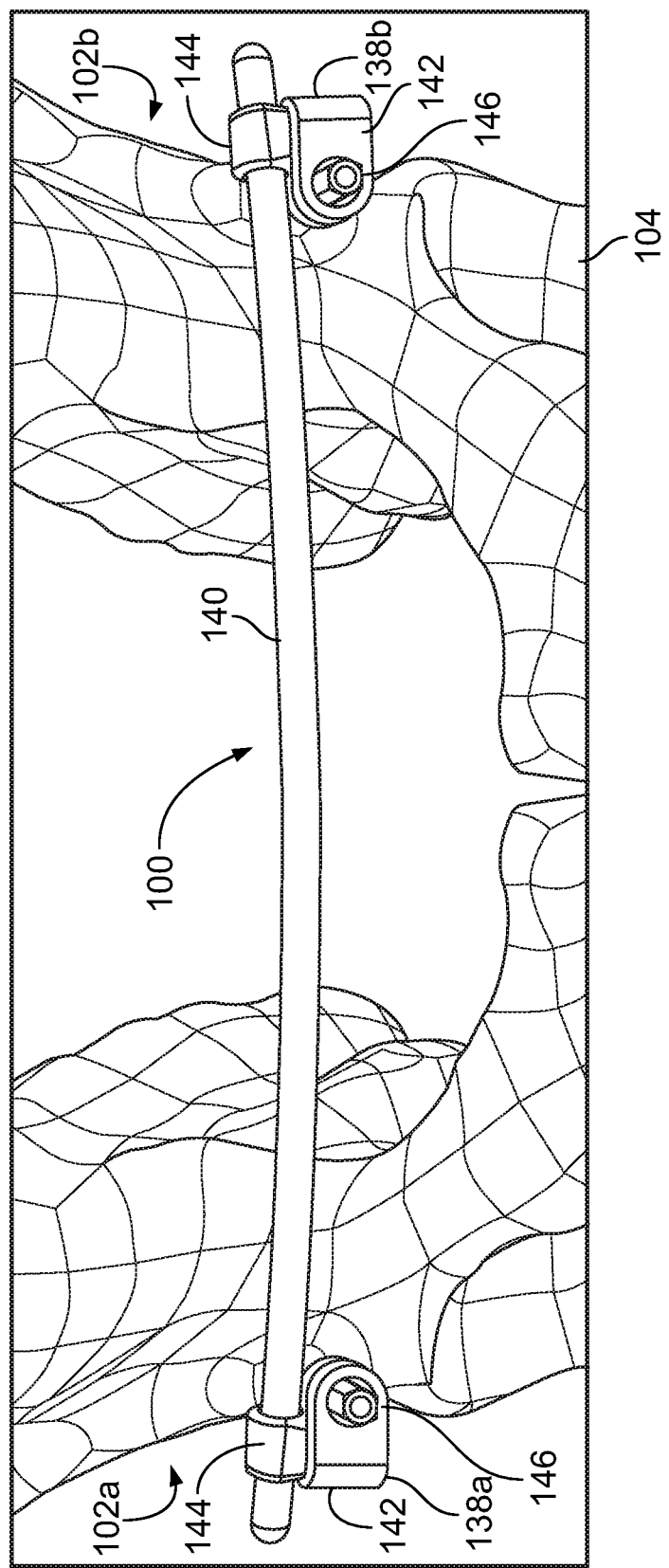
FIG. 1B illustrates a bend rod secured to the first and second clamps at a position that reduces a fracture in the pelvis.

Embodiments of the present application generally relate to a system and method of installation and/or removal of an internal pelvic fixator 100 in a portion of first side 102a and a portion of a second side 102b of a pelvis 104 of a patient, as shown, for example, by at least FIGS. 1A and 1B. For example, embodiments of the present application can be used in connection with at least stabilization of the anterior ring for pelvic fractures, among other applications. Further, the internal pelvic fixator 100 can be used in connection with the treatment of a variety of different types of pelvic fractures, such as, but not limited to, open or closed injuries, and anterior ring injuries with concurrent instability, including bilateral rami fractures, parasymphseal injuries, and fractures of the superior pubic root, among others. While embodiments herein are discussed with reference to one or more exemplary surgical processes for implanting an internal pelvic fixator 100, the operations illustrated for all of the processes in the present application are understood to be examples only, and operations may be combined or divided, and added or removed, as well as re-ordered in whole or in part, unless explicitly stated to the contrary.

Figure 2A:
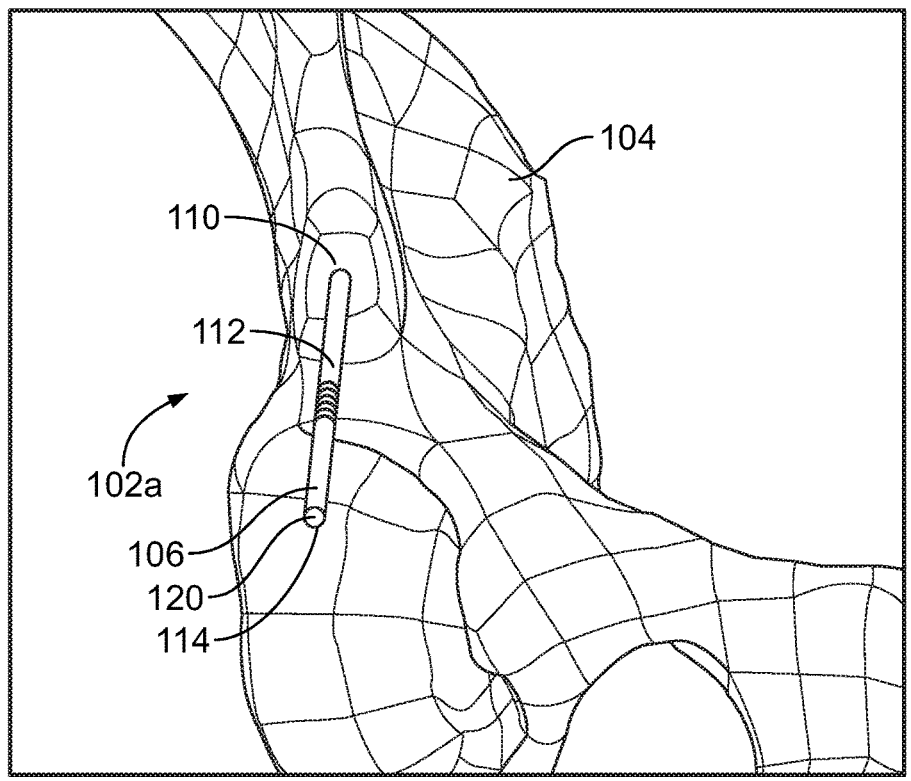
FIG. 2A illustrates a front side view of a guide being positioned adjacent to an anterior inferior iliac spine (AIIS) of a pelvis.
Figure 2B:
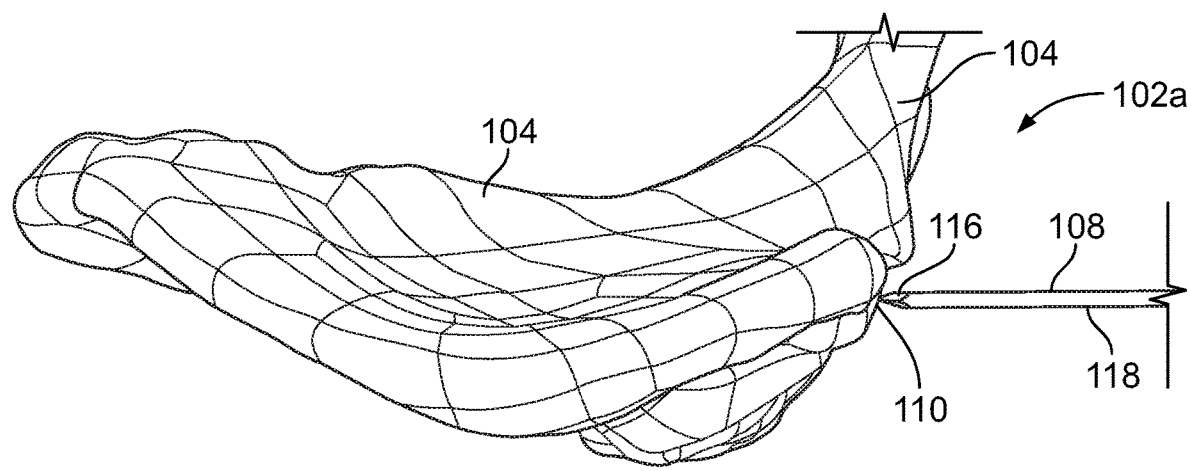
FIG. 2B illustrates a top side view of a guide wire being positioned adjacent to an AIIS of a pelvis.

FIGS. 2A and 2B illustrate a guide 106 and guide wire 108, respectively, being positioned to locate an anterior inferior iliac spine (AIIS) 110 on a first side 102a of the pelvis 104, such as, for example, a right or left side of the pelvis 104. According to certain embodiments, the guide 106 is cannulated. The guide 106 includes a guide wall 112 that generally defines a hollow inner region 114 of the guide 106. The hollow inner region 114 of the guide 106 is sized to receive at least the placement of a portion of the guide wire 108. Further, according to certain embodiments, the guide wire 108 is a graduated wire, and may have a variety of different shapes and sizes. For example, according to the illustrated embodiment, the guide wire 108 is a graduated wire having a diameter of approximately 2.9 millimeters (mm). Additionally, according to certain embodiments, in connection with, and/or after, locating the MIS 110, the orientation or alignment of the guide 106 and/or guide wire 108 relative to the AIIS 110 may be verified. For example, the orientation or alignment of the guide 106 and/or guide wire 108 may be verified. For example, the orientation or alignment of the guide 106 and/or guide wire 108 relative to the AIIS 110 may be verified via fluoroscopy.

Figure 3A:
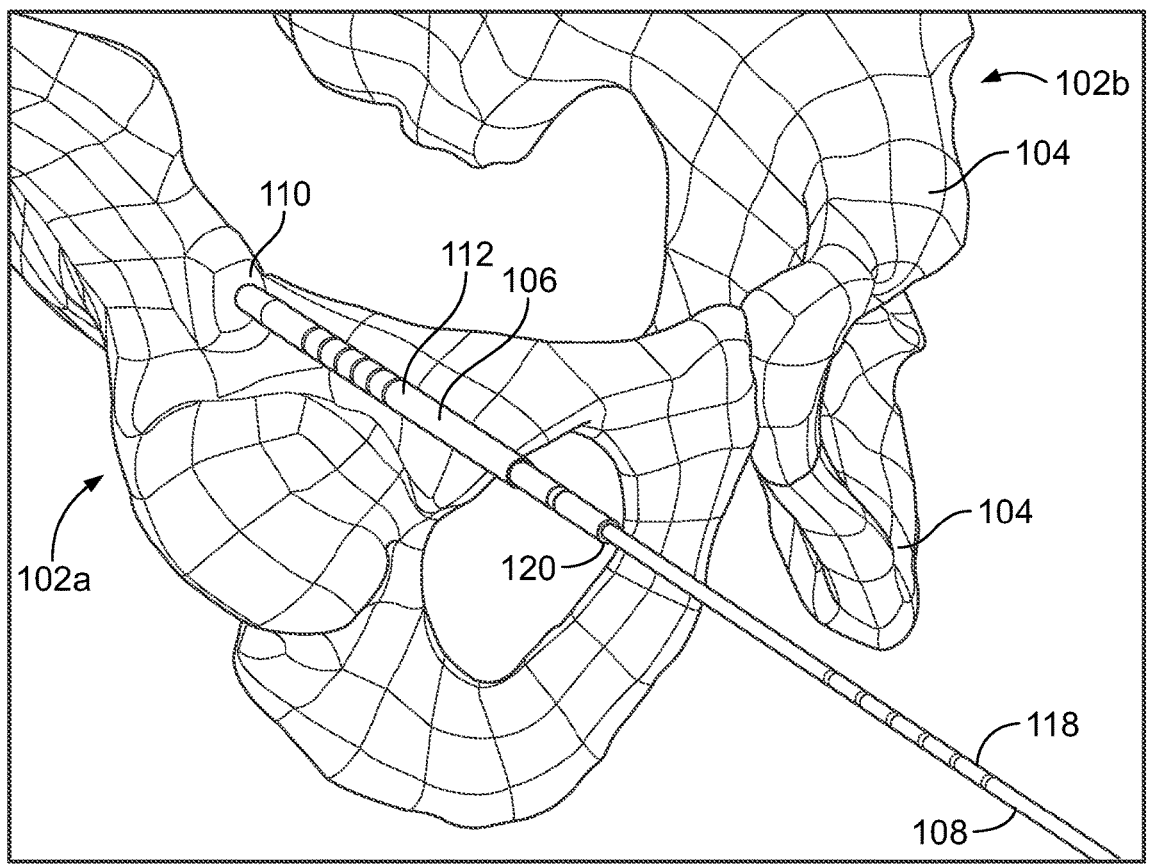
FIGS. 3A and 3B illustrate a top side perspective view and a side view, respectively, of a guide wire insert into a guide and the AIIS of a pelvis.
Figure 3B:
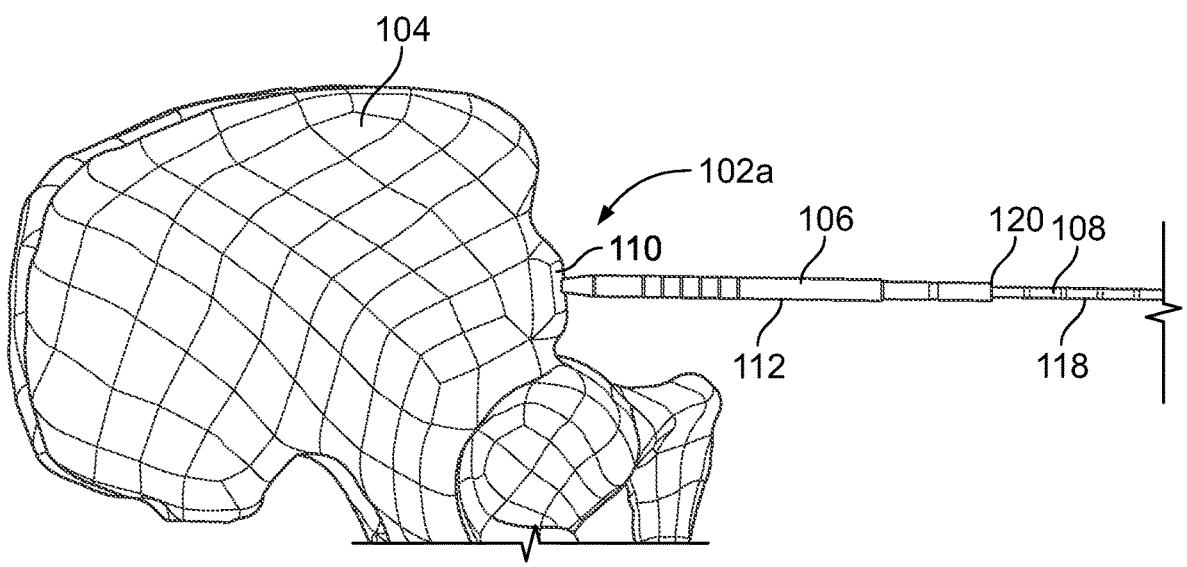

According to certain embodiments, with the AIIS 110 located, the guide 106 may be positioned to at least abut against the AIIS 110, if not at least partially penetrate into the AIIS 110. Further, the guide wire 108 may be inserted into the guide 106 such that a tip end 116 (FIG. 2B) of the guide wire 108 is positioned to be inserted into the AIIS 110. The tip end 116 of the guide wire 108 may be configured to at least assist in the ability of the guide wire 108 to be inserted into the AIIS 110. The guide wire 108 may continue to be inserted through the guide 106 until the guide wire 108 reaches a particular location or depth in the pelvis 104, as indicated by FIGS. 3A and 3B. For example, according to certain embodiments, the guide wire 108 may be driven under power until the tip end 116 of the guide wire 108 approaches the greater sciatic notch. Further, the depth at which the guide wire 108 has (or is) being inserted into the pelvis 104, as well as the trajectory or orientation of the guide wire 108 in the pelvis 104 may be monitored, detected, or otherwise verified, such as, for example, through the use of fluoroscopy.

Figure 4:
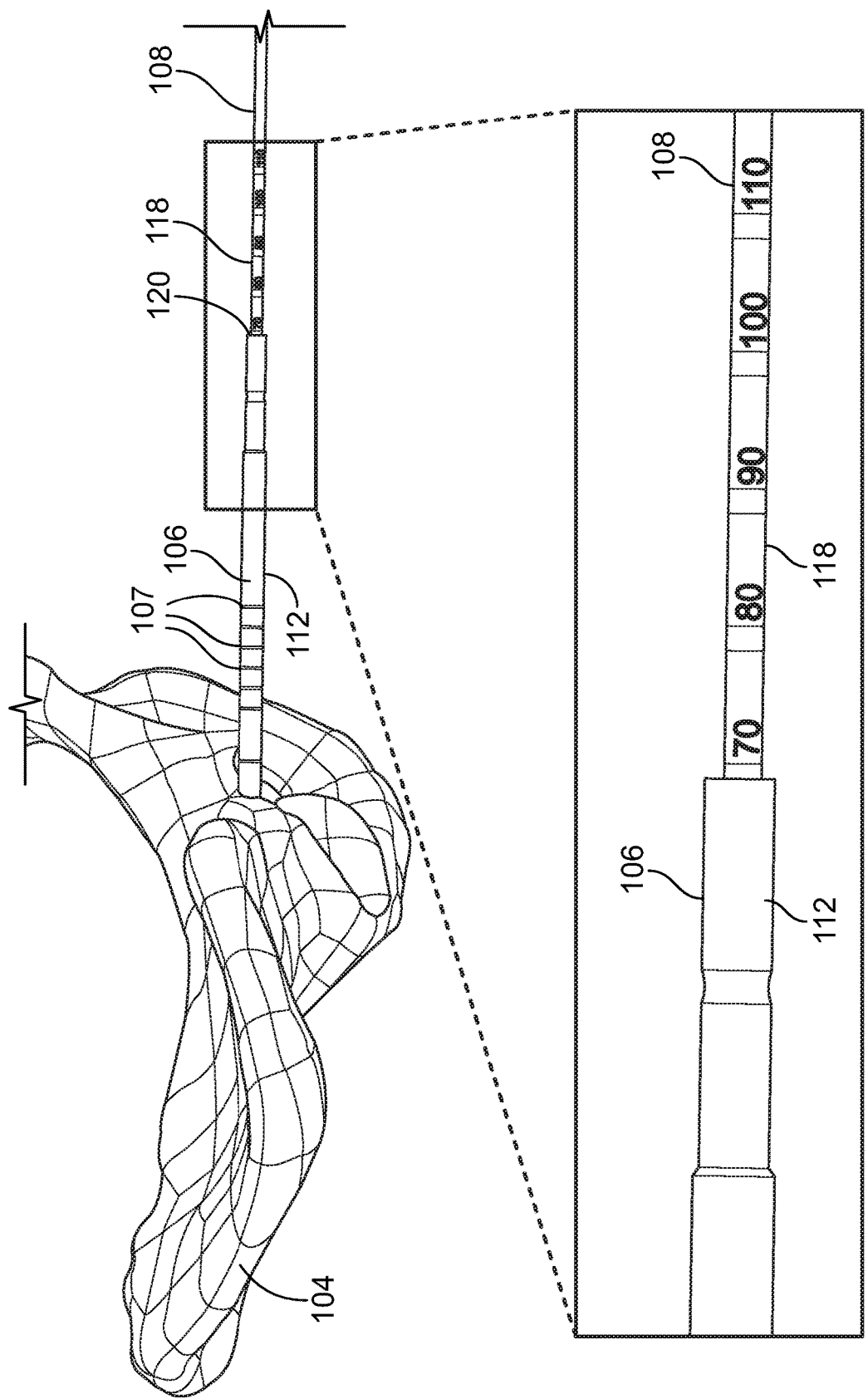
FIG. 4 illustrates an example of a guide wire that is inserted into a guide and an AIIS of a pelvis, with the guide wire identifying a screw working length measurement.

As indicated by FIG. 4, according to certain embodiments, the guide wire 108 may include indicia along an outer surface 118 of the guide wire 108. For example, as shown in FIG. 4, the indicium may include numeric values, such as, for example, values corresponding to a unit of measurement, including a metric value, among other values or representations. The indicia may be positioned on the outer surface 118 in a variety of different manners, including, for example, by laser marking, cutting, or etching, among other manners.

According to certain embodiments, the indicia on the outer surface 118 of the guide wire 108 may generally correspond to a length from an area around the tip end 116 of the guide wire 108 to a reference location on the guide 106, such as, for example, an end wall 120 of the guide 106. According to such embodiments, the indicia on the outer surface 118 of the guide wire 108 may provide an indication of the depth to which the guide wire 108 has been inserted into the pelvis 104. In the depicted embodiment, the indicia can provide an indication of the working or thread length of a screw 122 (FIGS. 5A-5C) that is to be inserted at that location in the bone of the pelvis 104. As one illustrated example, in FIG. 4 the indicium is a plurality of laser marked values on the guide wire 108 that are positioned relative to a reference location of the guide 106, which in this example is the end wall 120 of the guide 106, indicates at least that the guide wire 108 has been inserted to a depth in the pelvis 104 that may accommodate a screw 122 having a working or thread length of 70 millimeters (mm). According to certain procedures, the depth that has been attained into the bone by the guide wire 108 may be determined by removing the guide 106 and checking the indicia on guide wire 108. Additionally, or alternatively, the depth into the bone by the guide wire 108 may be attained via use of fluoroscopy. Further, according to certain embodiments, a depth gage may be placed over at least a portion of the guide wire 108 and may be used to measure, from an end of the guide wire 108 opposite of the tip end 116, a length of the guide wire 108 that did not enter into the bone. That information, in view of knowledge of the overall length of the guide wire 108, can provide an indication of the depth that the guide wire 108 extended into the bone.

A variety of different sized screws 122 can be utilized. For example, according to certain exemplary embodiments, the screw 122 can have a diameter of about 6.5 millimeters (mm) or about 8.0 millimeters (mm) and a length of about 60 millimeters (mm) to about 130 millimeters (mm), as measured from a base of a hexagonal drive feature to the tip of the screw 122, among other diameters and lengths. In addition to having a threaded portion, the screw can also include an unthreaded section along the length of the screw 122. The unthreaded section of the screw may be positioned and/or sized so as to prevent the threaded portion of the screw 122 from being at an exposed position outside the bone that could facilitate soft tissue irritation. Additionally, the unthreaded portion of the screw 122 can also provide a region where of, and/or used to install, the internal pelvic fixator 100 can connect or be coupled to the screw 122, and thus may help to prevent the screw 122 from being seated too close to the bone in a manner that could risk damage to the lateral femoral cutaneous nerve complex. According to certain embodiments, the unthreaded portion of the screw may extend a length of about 15 millimeters (mm) along the screw 123. Further, according to certain embodiments, the screws 122 used in mounting the internal pelvic fixator 100 to the bone are self-drilling and self-tapping. Additionally, the screw 122 can be cannulated to work with a graduated guide wire 108, such as, for example, a 2.9 millimeter (mm) graduated guide 108.

While the above mentioned processes have been discussed in terms of a first side 102a of the pelvis 104, such as the right or left side of the pelvis 104, the above-noted procedures may also be performed in connection with the other of the right or left side (referred to as the second side 102b) of the pelvis 104 and the associated AIIS 110.

Figure 6:
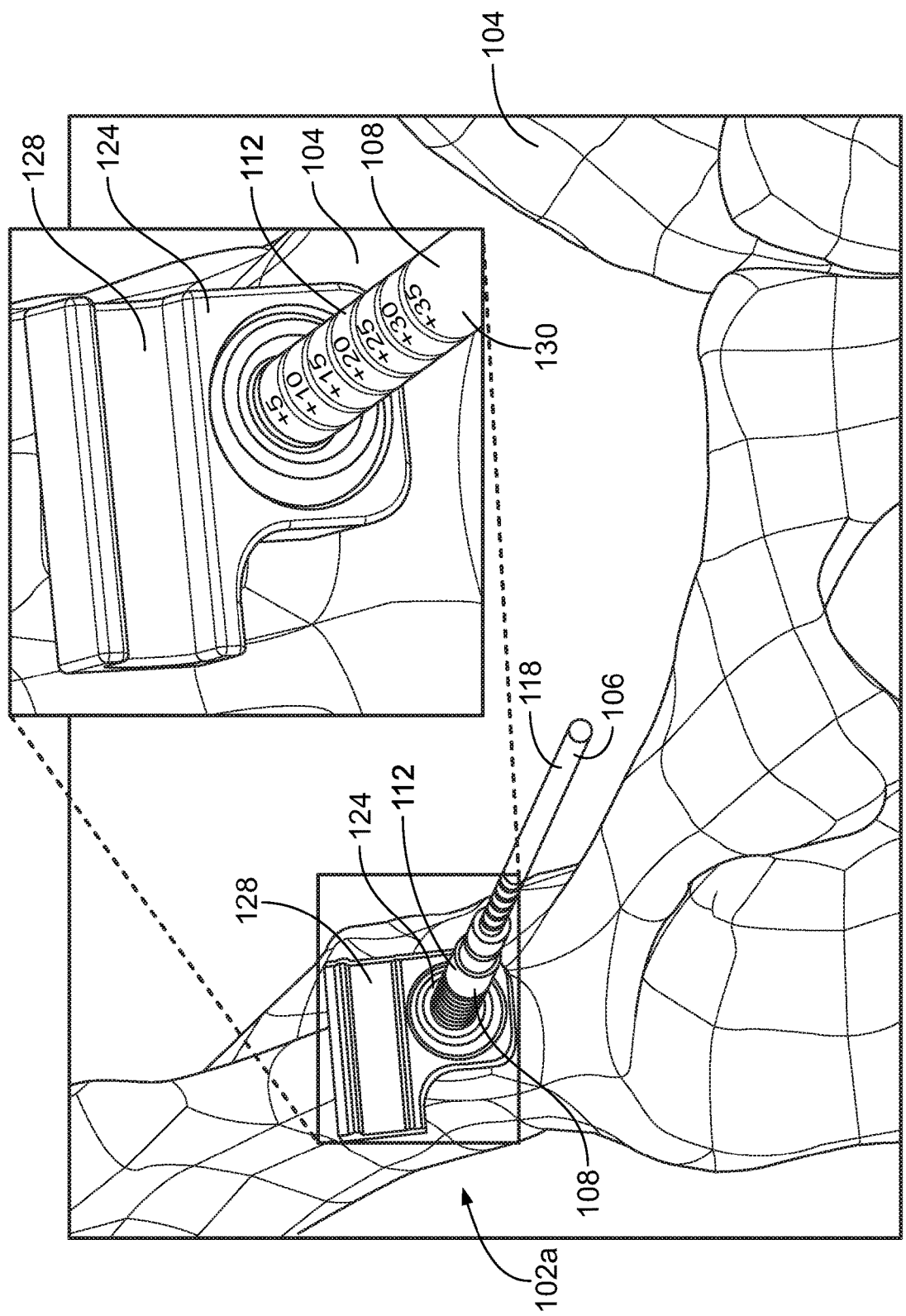
FIG. 6 illustrates a side view of a right side bend rod template positioned about a guide.
Figure 7:
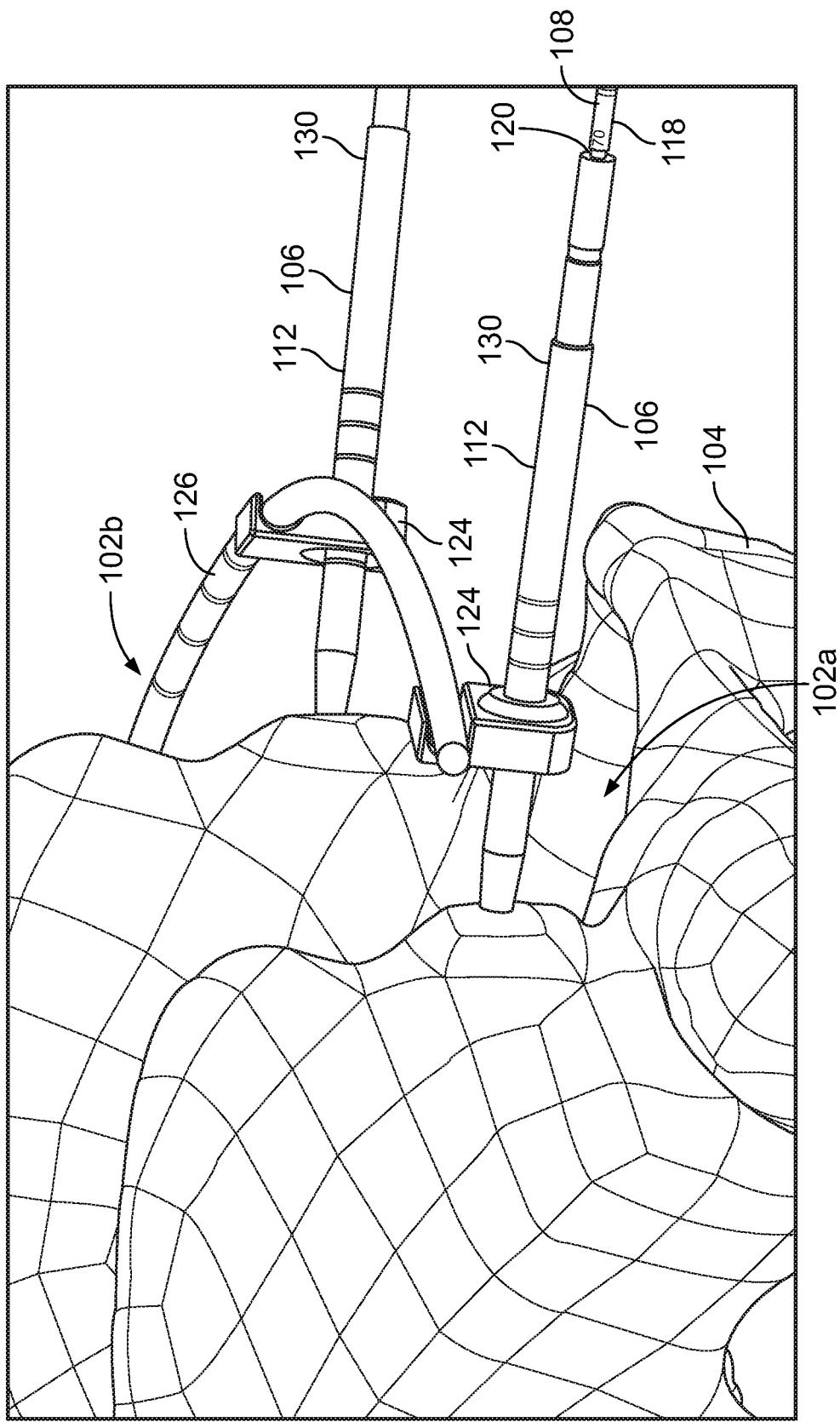
FIG. 7 illustrates a side perspective view of a template rod positioned in right and left side bend rod templates that are positioned along a portion of guides that house guide wires.

Referencing FIGS. 6 and 7, a bend template rod 126 may utilize a rod bender to match an abdominal contour of the patient. According to an exemplary procedure, use of the rod bender can include coupling a rod offset tool 124 to the guide wires 108 on the first and second sides 102a, 102b of the pelvis 104. For example, according to certain embodiments, the rod offset tool 124 can include an orifice sized to accommodate passage of the rod offset tool 124 over the guide wire 108 and guide 106. The rod offset tool 124 also includes a template channel 128 that is sized to receive placement of a portion of the template rod 126. For example, FIG. 6 illustrates the rod offset tool 124 for the "RIGHT" side of the patient that has a template channel 128 that accommodates placement of a first end 127 of the template rod 126 (FIG. 7). FIG. 7 demonstrates that another, second rod offset tool 124 is portioned over another guide 106 on the other side 102b of the patent, such as the left side of the patient, with the rod offset tool 124 for the other, or left side, of the patient having a template channel 128 that accommodates placement of another end or portion of the template rod 126. Further, the template rod 126 may have a construction that accommodates the shaping of the rod 126 by an operator or surgeon to generally conform to the anatomy of the patient. For example, according to certain embodiments, the template rod 126 may have a size, such as, for example, a diameter, and be constructed from a material, including, but not limited to, aluminum, that can accommodate the bending or shaping of the template rod 126 manually by an operator or surgeon, and/or via use of a rod bender.

The rod offset tools 124 may be positioned such that the template rod 126 is located superior and lateral to an adjacent screw that will be implanted or driven into the AIIS 110 at generally the location that the associated guide wire 108 has been inserted into the pelvis 104. With the rod offset tools 124 positioned, the template rod 126 may be inserted beneath the tissues of the patient and positioned in the template channels 128 of the rod offset tools 124, as shown in FIG. 7. The position of the template rod 126 may then be adjusted, such as, for example, adjusting the location of the rod offset tools 124 about the guide 106 until the template rod 126 is positioned at a selected location. Determination of the selected location for the template rod 126, and thus the rod offset tools 124, may involve consideration of a variety of factors. For example, according to certain embodiments, the presence of skin creasing in the skin of the patient above the template rod 126 may indicate that the template rod 126 is placed too deep into the patient. Further placement of the template rod 126 at a location that is too deep may cause compression of the Sartorius muscle. Additionally, a determination may be made as to whether the patient will have adequate skin coverage at the site of the implanted or driven screw(s). In the event there may not be adequate skin coverage, an alternative treatment for addressing the patient's injury may be considered. If the template rod 126 visually protrudes beneath the skin of the patient in the middle of the abdomen, consideration may be given to removing the template rod 126 and adjusting the curvature of the template rod 120 or inserting the screws 123 more deeply.

When a selected position for the template rod 126 has been obtained, the location of rod offset tools 124 relative to the corresponding guide 106 may be detected in connection with determining a rod offset measurement or value. For example, according to certain embodiments, the guide wall 112 of the guide 106 may include indicia on an outer portion 130 of the guide wall 112 that provides an indication of the location of the rod offset tool 124 relative to the guide 106. Such indicia may be provided in a number of manners, including, for example, markings, recesses, or other changes or variations in size or appearance along the outer portion 130 of the guide wall 112. However, according to certain embodiments, a default rod offset value or measurement may be utilized that corresponds to a distance an implant rod will be from pelvis. Such a default rod offset value or measurement may be utilized to minimize the risk of LFCN impingement. With the rod offset measurement or value determined and/or the template rod 126 positioned, the guide 106 and rod offset tools 124 may be removed from the patient. Further, according to certain embodiments, while the guide 106 and rod offset tools 124 may be removed from the patient, the template rod 126 generally may remain in place.

Alternatively, according to other embodiments, rather than, or in addition to, using offset tools 124, the guide 106, or another or different guide, can include indicia 107 indicative of a position between the pelvic bone and a location for another component of the internal pelvic fixator 100, as shown by at least FIG. 4. According to certain embodiments, such a position, which can be referred to as an offset position, can, for example, provide a reference location that is the distance between the pelvic bone, another anatomical feature of the patient, and/or another component of the internal pelvic fixator 100, including, but not limited to, a bone screw 122. Further, according to certain embodiments, the guide may include an opening that is sized to receive the guide wire 108. For example, as previously mentioned, according to certain embodiments, the hollow inner region 114 of the guide 106 can be sized to accommodate placement of the guide 106 about the guide wire 106. Thus, according to certain embodiments, with the guide 106 positioned about the guide wire 108 and against the pelvis bone 104, the indicia may provide an indication of the potential distances, or offset positions away from the pelvic bone for the positioning of a template rod 126, implant rod 140, and/or first and second clamps 138a, 138b. Further, while the indicia 107 in FIG. 4 is illustrated as lines, a variety of other types or combinations of indicia, including, shapes, graphics, and/or information can be utilized.

Figure 5C:
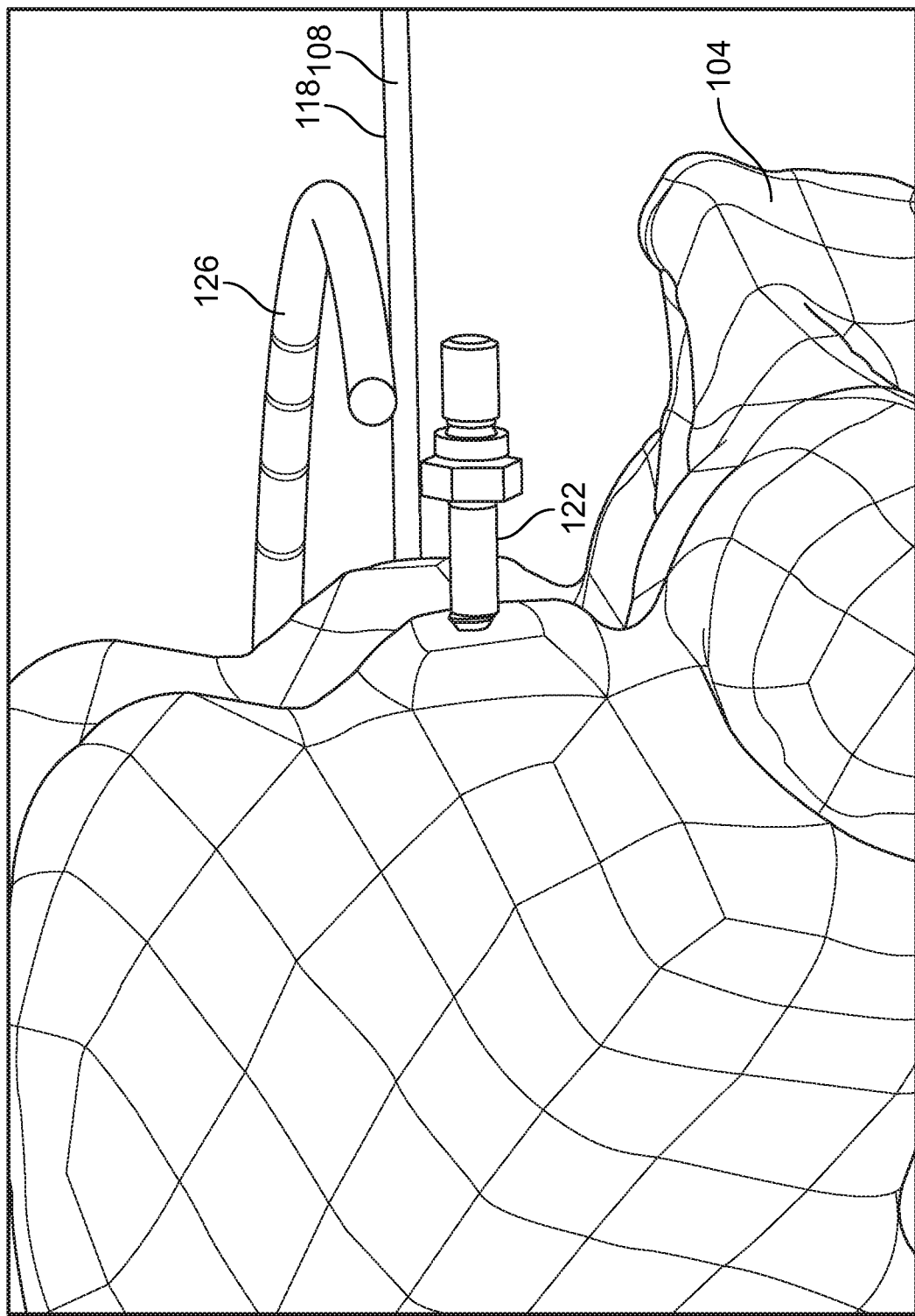
FIG. 5C illustrates a side view of the screw of FIG. 5B that has been driven into the AIIS of a pelvis and after removal of the guide wire and screwdriver.

Referencing FIGS. 5A-5C, a screw 122 may be inserted over the pelvis 104 at each of the locations of the guide wires 108. According to certain embodiments, the previously determined rod offset measurement or value may be utilized in the selection of a depth stop 132, which may be used to influence the depth to which the screw 122 will be inserted into the pelvis 104. According to certain embodiments, the depth stop 132 may be placed over the guide wire 108 that is adjacent to the pelvis 104, and provide an abutment that limits the proximity to which a driver, such as a screwdriver 134, among other drivers, that is driving the screw 122 may come to the pelvis 104, thereby limiting the depth to which the screwdriver 134 may drive the screw 122 into the bone of the pelvis 104. The rod offset measurement or value may also be utilized with a working length value for the screw 122 in determining what length of screw 122 is to be utilized. In at least certain instances, the working length of the screw 122 may correspond to a length of at least a portion of the screw 122 that is to extend outside of bone of the pelvis 104 so as to be positioned or able to engage with other components of the internal pelvic fixator 100.

According to such an embodiment, with the depth stop 132 positioned about the guide wire 108, the screw 122 may be positioned over the guide wire 108. Further, the screwdriver 134 may engage the screw 122, which may, according to at least certain embodiments, involve the screwdriver 134 also being positioned about the guide wire 108. The screwdriver 134 may then be operated to drive the screw 122 until the screw 122 is inserted to a selected depth into the bone. Again, according to certain embodiments, the screwdriver 134 may be operated until the screwdriver 134 contacts the depth stop 132. Further, according to certain embodiments, the screw 122 may inserted into a depth in the bone that permits at least a portion of the thread 136 of the screw 122 to remain outside of the bone of the pelvis 104. Thus, according to such an embodiment, all threads 136 of at least the area of the screw 122 that is being driven into the bone are not below the surface of the bone. With the screw 122 implanted or driven into the bone, the screwdriver 134, depth stop 132 and guide 106 may be removed from the guide wire 108, and the guide wire 108 may be removed from the patient. Although the above operations have been discussed with respect to one screw 122 on one side 102a of the pelvis 104, the same procedures may be utilized to implant or drive another screw 122 into the AIIS 110 at the other side 102b of the pelvis 104.

Further, according to certain embodiments, indicia 135 (FIGS. 5A and 5B) can be included on the screwdriver 134 that provides an indication of an offset position between the pelvic bone, another anatomical feature of the patient and/or another component of the internal pelvic fixator 100, including, but not limited to, a bone screw 122 that can at least assist in driving the screw 122 to an appropriate depth. While the indicia 135 is illustrated as a plurality of lines, a variety of different types, or combinations of types, of indicia can be incorporated, including, but not limited to, indicia that is in the form of one or more graphics, among other shapes or representations.

Figure 8A:
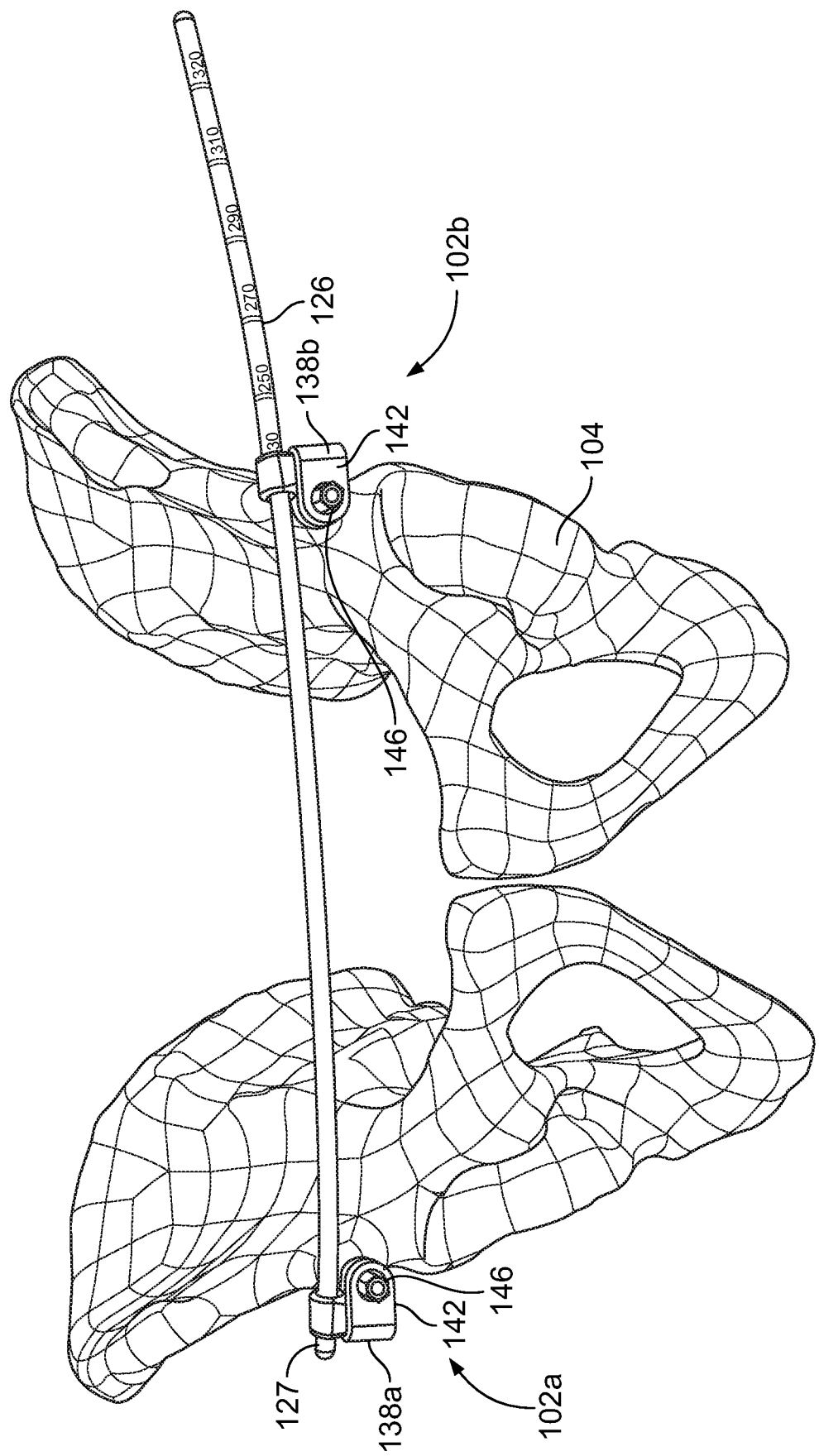
FIG. 8A illustrates a front view of portions of a template rod positioned in first and second clamps that are coupled to the screws that are driven into the pelvis.
Figure 8B:
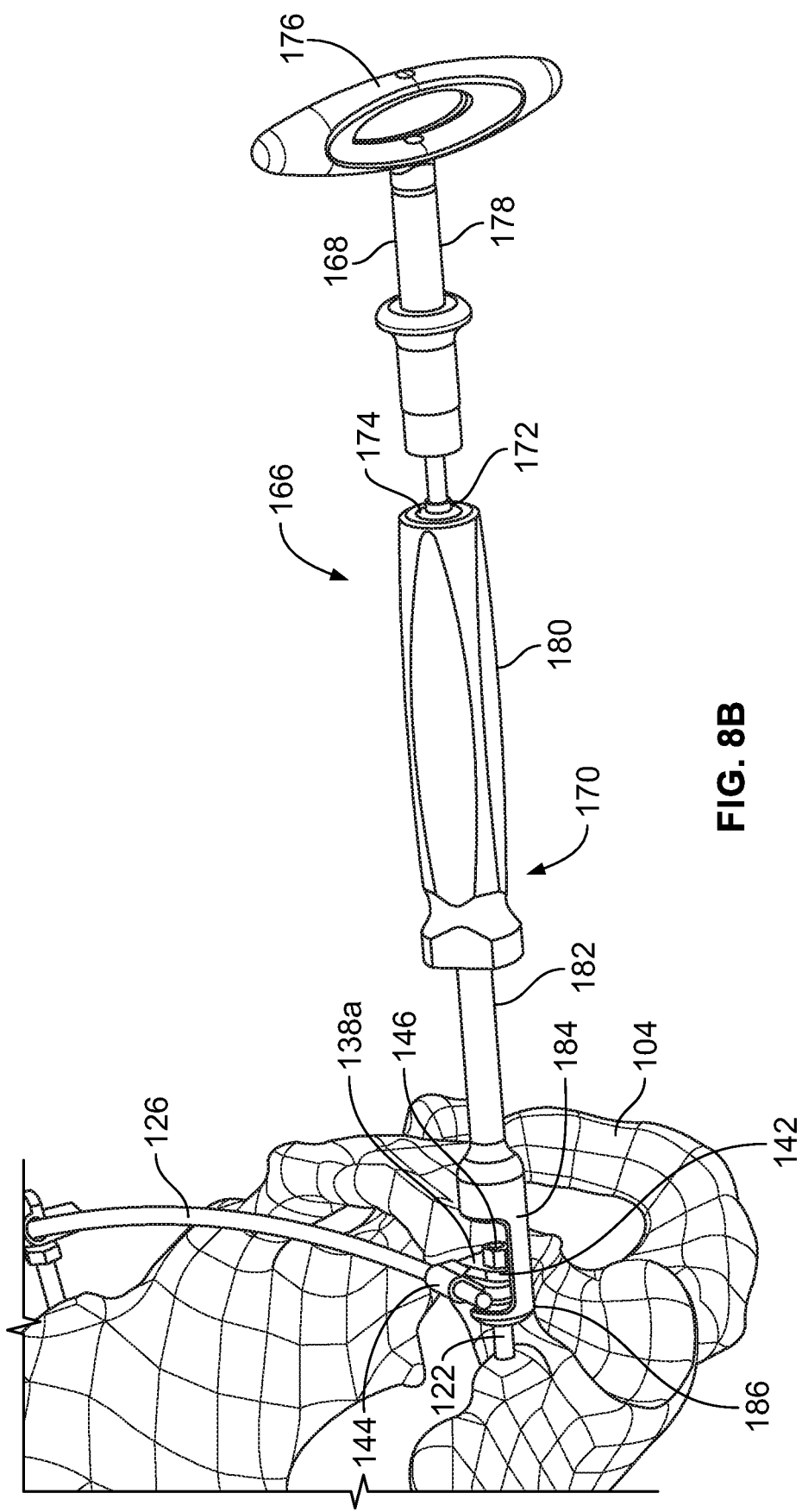
FIG. 8B illustrates a side view of a T-shaped handle being connected to a first joystick that is being coupled to a first screw.
Figure 9:
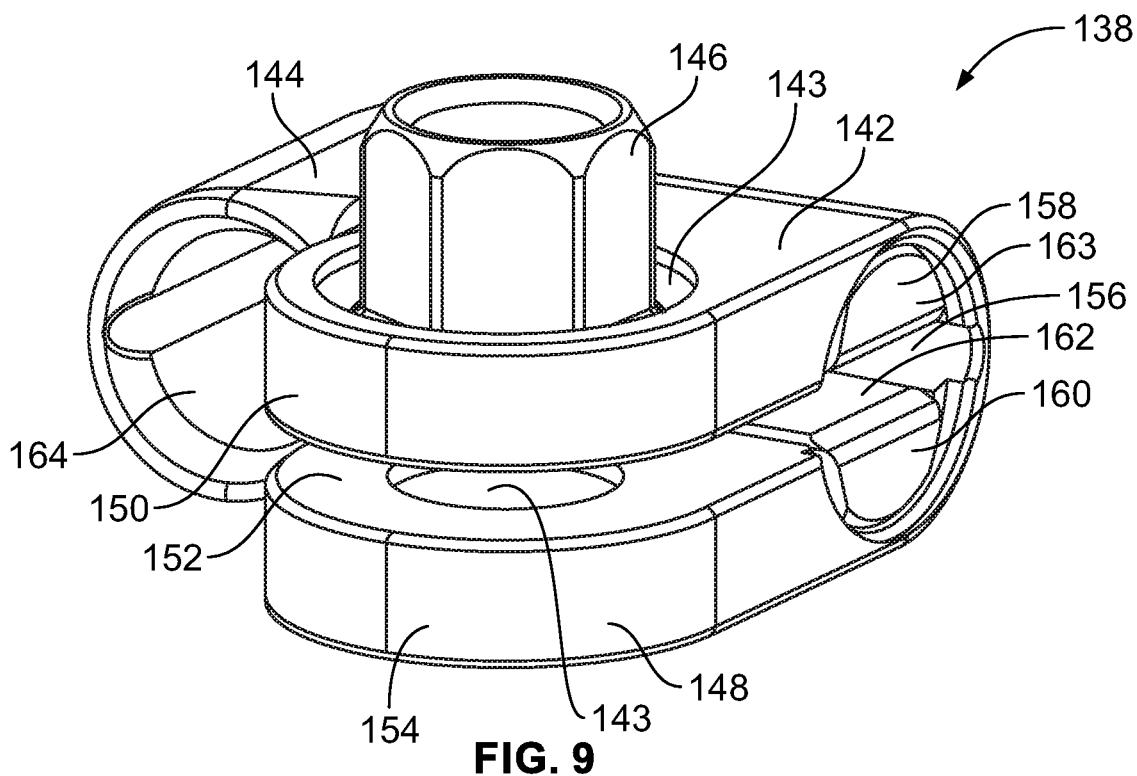
FIG. 9 illustrates a first side perspective view of an exemplary embodiment of a clamp.
Figure 10:
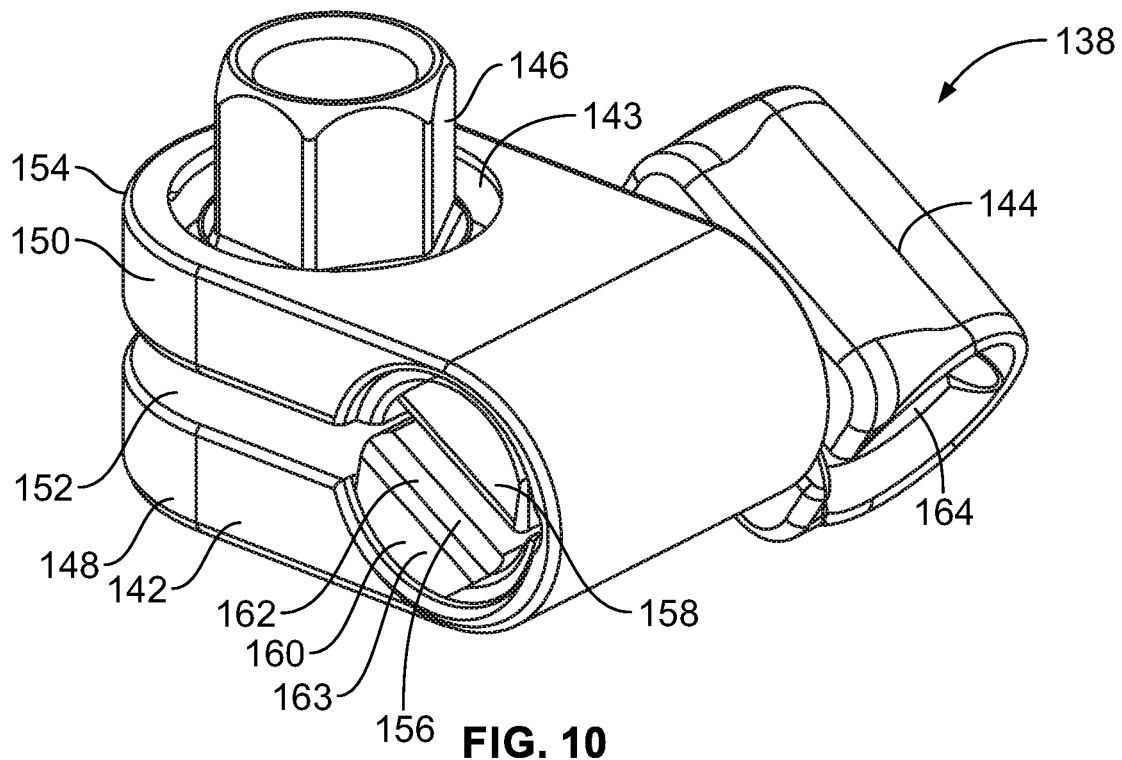
FIG. 10 illustrates a second side perspective view of an exemplary embodiment of a clamp.
Figure 11:
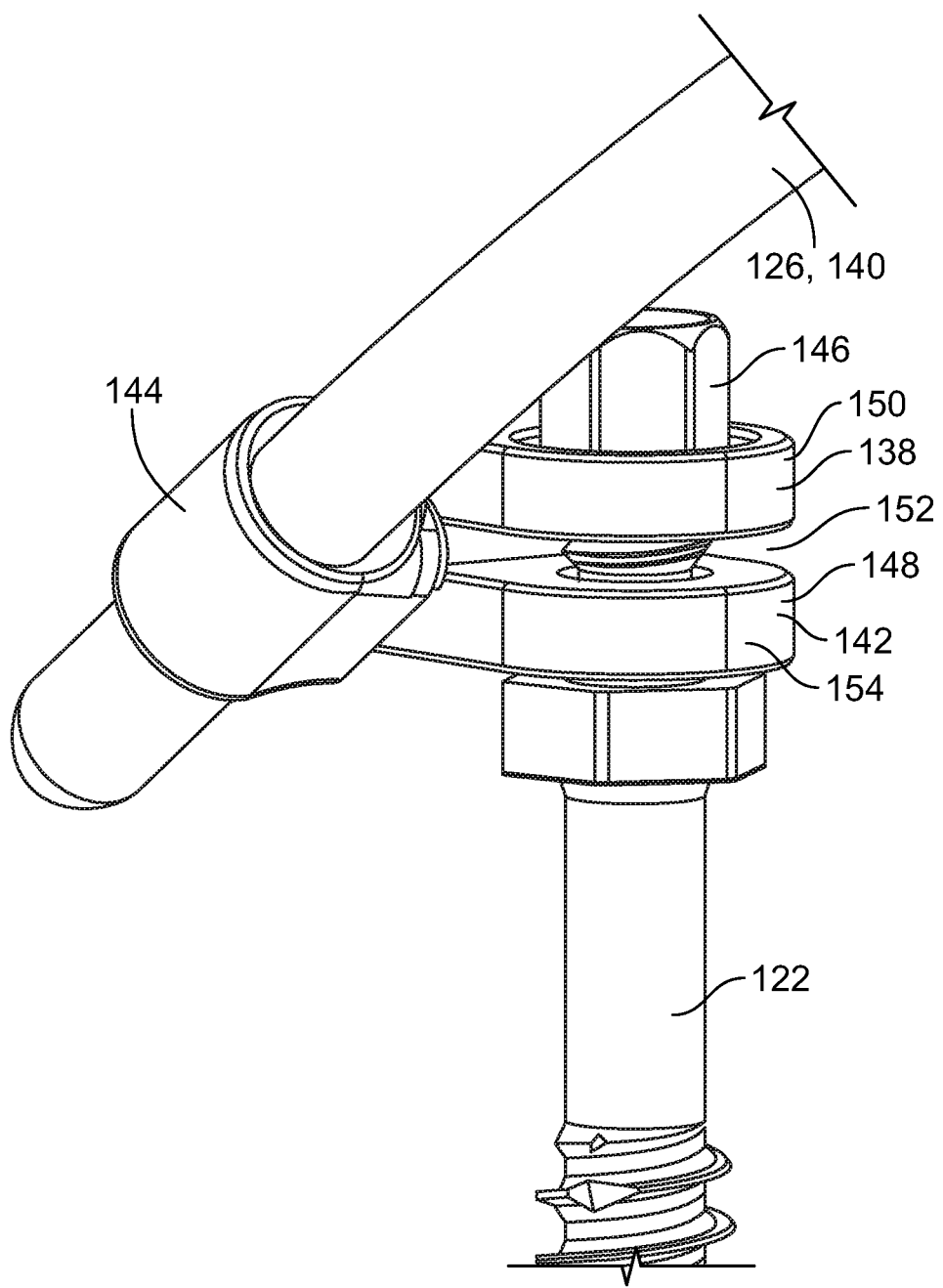
FIG. 11 illustrates the clamp shown in FIGS. 9 and 10 engaged with a screw and a template or implant rod.

FIGS. 8A to 8B illustrate first and second clamps 138a, 138b engaging different sections of the template rod 126, and which each engage a screw 122 that has been implanted or driven into a the pelvis 104. Additionally, an exemplary embodiment of one type of clamp 138 that may be utilized is shown in FIGS. 9-11. The clamps 138a, 138b are configured to be adjustable in orientation so as to accommodate differences in patients' anatomies, and moreover, accommodate for variations in the relative locations and/or orientation of at least the template rod 126 (and the later inserted implant rod 140, as shown in at least FIG. 12 and as discussed below) and the adjacent screw 122.

According to the illustrated embodiment, each clamp 138 may include a screw clamp 142, a rod clamp 144, and a clamping nut 146. Further, the screw clamp 142 may have a generally unitary body and include features that enable the screw clamp 142 to engage with an adjacent screw 122, the rod clamp 144, and the clamping nut 146. For example, according to the illustrated embodiment, the screw clamp 142 includes a first screw clamping segment 148 and a second screw clamping segment 150. The first and second screw clamping segments 148, 150 are separated from each other by a gap 152 that extends from a first end 154 of the screw clamp 142 to a clamping bore 156 that is sized to receive insertion of the rod clamp 144. Moreover, the clamping bore 156 is configured to selectively exert a clamping force on the rod clamp 144 that may prevent rotational displacement of the rod clamp 144 about the clamping bore 156 when the screw clamp 142 is displaced to a clamped position.

The screw clamp 142 further includes an aperture 143 that extends through the first and second screw clamping segments 148, 150. The aperture 143 is sized to receive insertion of at least the clamping nut 146. Further, the aperture 143 and/or the clamping nut 146 may be configured to retain the clamping nut 146 within, or engagement with, the aperture 143 of the screw clamp 142, as shown in at least FIGS. 9 and 10. Such a feature may further accommodate rotation of the clamping nut 146 independent of rotation of the screw clamp 142, and vice versa. Thus, according to the depicted embodiment, the screw clamp 142 has a 360.degree. range of motion about a central longitudinal screw axis of the screw 122 at least until the clamping nut 146 is tightened onto the mating external thread on the screw 122. Additionally, according to certain embodiments, tightening of the clamping nut 146 locks a tapered connection between the screw clamp 142 and the screw 122 to lock rotation of the screw 122 about the screw axis of the screw 122.

Similar to the screw clamp 142, the rod clamp 144 includes a first rod clamping segment 158 and a second rod clamping segment 160 that are separated by a slot 162. The slot 162 extends from a first end 163 of the rod clamp 144 to a clamping orifice 164 of the rod clamp 144. Further, at least a portion of the first and second rod clamping segments 158, 160 are configured for placement in the clamping bore 156 of the screw clamp 142. Additionally, the first and second rod clamping segments 158, 160 are also configured for rotational displacement within the clamping bore 156 of the screw clamp 142 at least when the screw clamp 142 is in an untightened condition. Thus, according to certain embodiments, the rod clamp 144 may have a 360.degree. range of motion about the clamping bore 156, and thus relative to the screw clamp 142, at least when the clamping bore 156 of the screw clamp 142 is in an at least partially untightened condition.

The clamping bore 156 of the screw clamp 142 may compress the rod clamp 144, when the clamping nut 146 is tightened about the screw 122. Moreover, as the clamping nut 146 is tightened, the first and second screw clamping segments 148, 150 may be brought into closer proximity to each other, thereby reducing the width of the gap 152 therebetween. Such displacement of the first and second screw clamping segments 148, 150 may reduce a size of the clamping bore 156 such that the clamping bore 156 exerts a compressive force on the first and second rod clamping segments 158, 160 that brings the first and second rod clamping segments 158, 160 in closer proximity to each other, thereby reducing the width of the slot 162 therebetween. Further, such compressive force(s) may provide a force sufficient to prevent the rotatable displacement of the first and second rod clamping segments 158, 160 about the clamping bore 156, and thus secure the rod clamp 144 at a position relative to the screw clamp 142. Additionally, the compressive force provided by the displacement of the first and second rod clamping segments 158, 160 may reduce a size of the clamping orifice 164 of the rod clamp 144 so as to secure the rod clamp 144 to the template rod 126 (or implant rod 140) in a manner that prevents rotational displacement of the template rod 126 (or implant rod 140) relative to the rod clamp 144. Thus, the rod clamp 144 has an allocation for the template rod 126 (or implant rod 140) to pass through the rod clamp 144 that is closed by the compression of the screw clamp 142 during tightening of the clamping nut 146. Further, according to other embodiments, the clamping orifice 164 and/or other portions of the rod clamp 144 may be configured in manner that prevents the clamping orifice 164 from being clamped onto an implanted or driven screw 122.

According to certain embodiments, the rod clamp 144 has features that prevent disassociation of the rod clamp 144 from the screw clamp 142 while allowing for 360 degrees of rotation of the rod clamp 144 relative to the screw clamp 143 when the clamp 138 has not be compressed. Additionally, the central longitudinal axis screw axis of the screw 122 and the axis of the rod clamp 144 to screw clamp 142 connection are generally perpendicular, with the resulting combination of orthogonal 360.degree. ranges of motion resulting in a complete 360.degree. spherical range of engagement between the template rod 126 (or implant rod 140) and the screw 122. Moreover, such a design provides single tightening action, such as via use of the clamping nut 146, to lock two rotational axes simultaneously while granting 360.degree. spherical range of motion between mating components. Further, the connection between the rod clamp 144 and the screw clamp 142 in the depicted embodiment may accommodate the template rod 126 or implant rod 140 being clamped on either side of the screw 122, such as the superior or inferior sides, without additional left/right components.

According to other embodiments, the clamp 138 may include features that may enhance the clamping strength of the screw clamp 142 and/or the rod clamp 144. For example, according to certain embodiments, the screw clamp 142 and/or the rod clamp 144 may include ridges, altered surface roughness or treatments, non-circular (e.g., ovoid, tapered) connections, and/or multiple locking screws that compress the screw clamp 142 and rod clamp 144, either together or independently. Further, according to other embodiments the connections are non-symmetric.

Figure 13A:
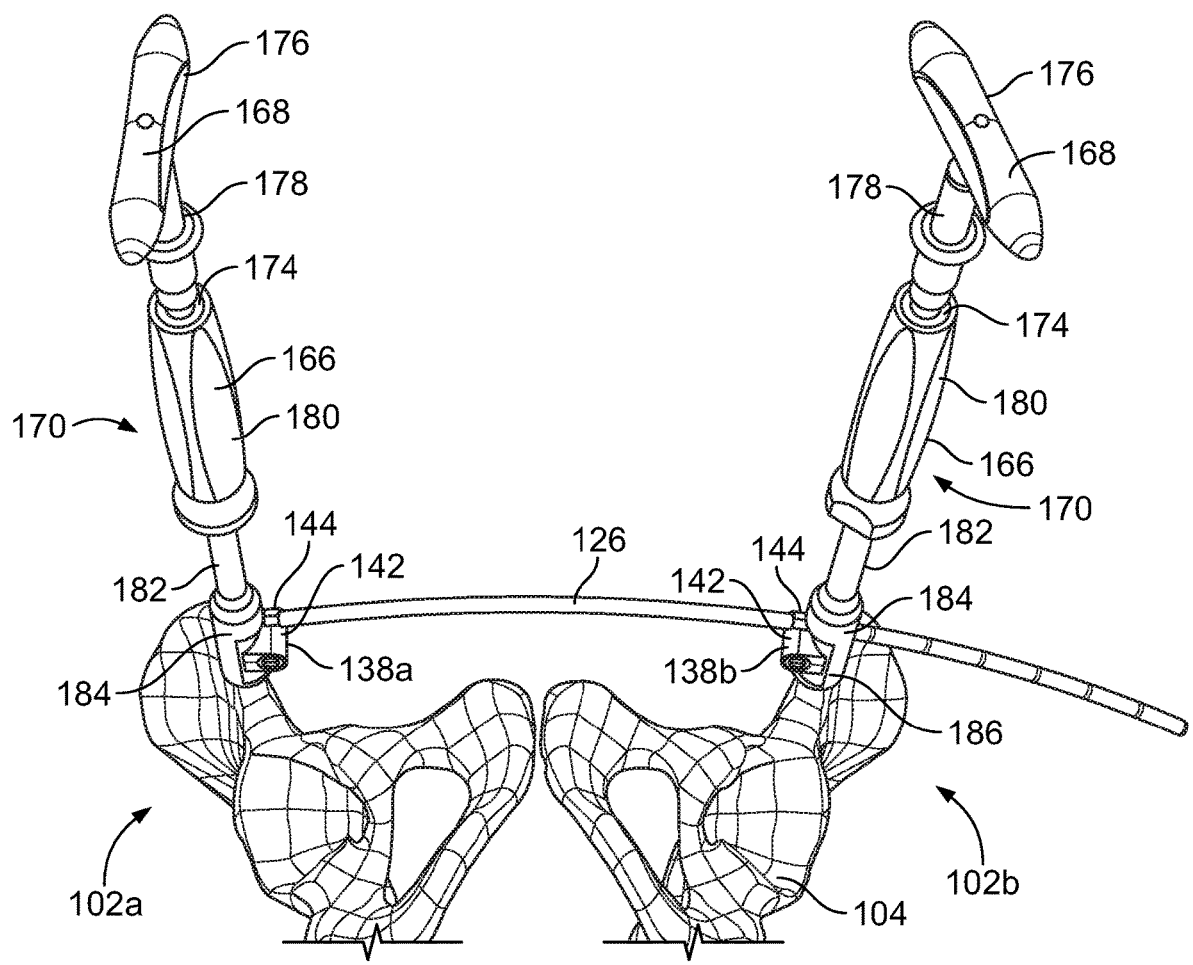
FIG. 13A illustrates first and second joysticks secured to first and second screws, respectively, and positioned to tighten an adjacent clamping nut in connection with manipulating bone fragments to selected positions.
Figure 13B:
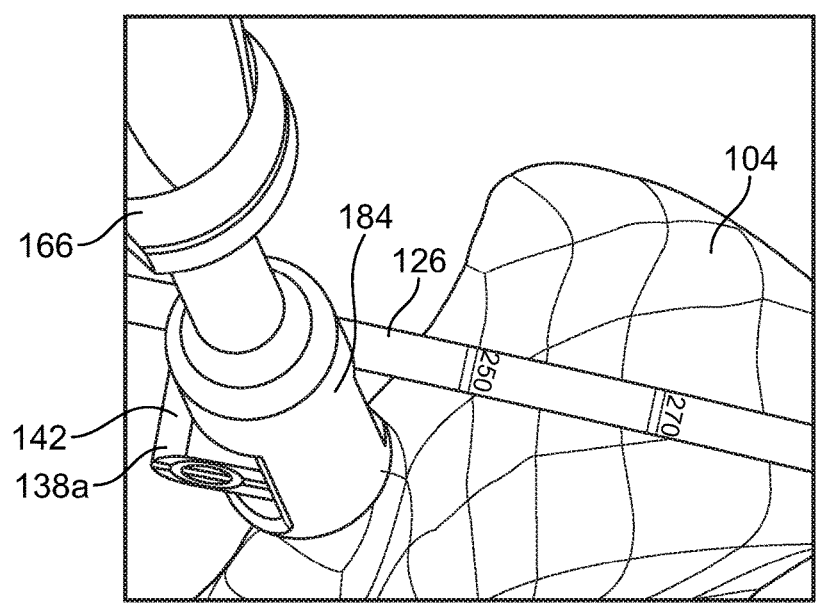
FIG. 13B illustrates use of a template marking on a template rod in connection with the determination of an implant rod size when a fracture size is reduced.

As indicated by at least FIGS. 13A and 13B, the template rod 126 may be inserted into the clamping orifice 164 of each of the clamps 138a, 138b. The clamping nut 146 of each of the clamps 138a, 138b may also engage an adjacent screw 122 that is implanted or driven into bone of the pelvis 104. According to certain embodiments, when the clamps 138a, 138b are being placed into engagement with the screws 120 via engagement of the respective clamping nut 146 and screw 120, the clamps 138a, 138b may be oriented such that the clamps 138a, 138b are superior and lateral to the associated screw 122.

According to certain embodiments, the clamps 138a, 138b may be secured to their respective screw 122 through the use of a joystick 166, as shown in at least FIGS. 1A, 8B, 12, and 13A-15B. The joystick 166 may include a handle 168 that may be secured to a first end 174 of a body portion 170 of the joystick 166 by a connector 172, such as, for example, an AO connection, among other connections and or fasteners. The handle 168 can include grip portion 176 that provides a location at which a user may operably grip the handle 168. According to certain embodiments, the grip portion 176 may outwardly extend from two or more sides of a shaft portion 178 of the handle 168 so that the handle 168 is generally T-shaped. Additionally, as discussed in more detail below, the handle 168 may be axially displaceable from a first position, as shown for example in FIG. 8B, to a second position, as shown, for example, in FIG. 17A, relative to at least a portion of the body portion 170 of the joystick 166 so that an inner section of the joystick 166 may be moved into, or away from, engagement with the clamping nut 146 of the associated clamp 138a, 138b. Additionally, according to certain embodiments, at least the handle 168 of the joystick 166 may be rotatably displaceable relative to the body portion 170 of the joystick 166.

According to certain embodiments, the body portion 170 of the joystick 166 may include a tubular segment 182 that extends from a grip section 180 of the body portion 170. The grip section 180 of the body portion 170 may be configured to be gripped by a hand of a user of the joystick 166, such as, for example gripped by a first hand of a user while the user's second hand rotatably displaces the handle 168 relative to the body portion 170. While the grip section 180 may have a variety of different shapes and configurations, according to the depicted embodiment, the grip section 180 generally has a combination of generally rectangular shapes, recesses and/or chamfers, among other shapes and configurations. Additionally, the grip section 180, or a portion of the body portion 170 within the grip section 180, may be configured for engagement with the connector 172 of the handle 168. Additionally, at least a portion of the grip section 180 may be sized to accommodate slidable displacement of a portion of the handle 168 into, and out of, the grip section 180 as the handle 168 is displaced between the first and second positions.

According to certain embodiments, the tubular segment 182 of the body portion 170 may extend to an engagement body 184 at a second end 186 of the body portion 170. The tubular segment 182 has a variety of different shapes and sizes, such as, for example, being generally cylindrical in shape. Additionally, the tubular segment 182 may be sized to accommodate slidable displacement of at least a portion of an engagement member 188 into/from the tubular segment 182 as the handle 168 is displaced between the first and second positions.

Figure 15A:
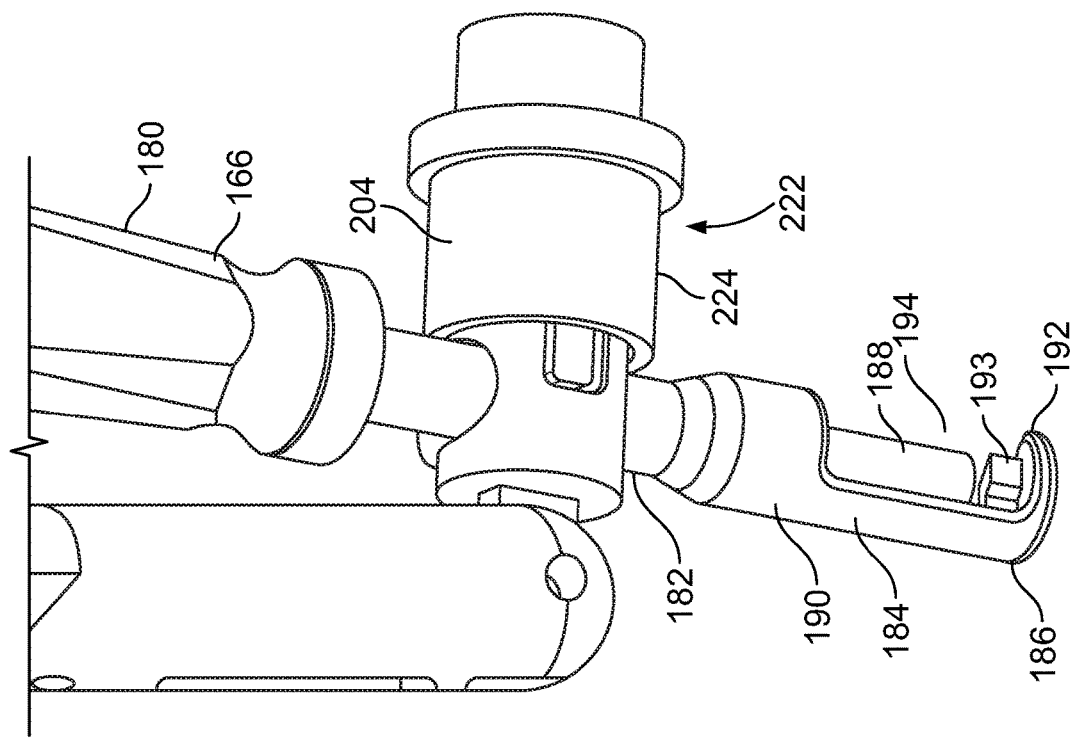
FIGS. 15A and 15B illustrate a coupler of a reduction holder mechanism shown in FIG. 16 being in a first, unlocked position and second, locked position, respectively, relative to a joystick and the engagement member of the joystick at a second, extended position.
Figure 15B:
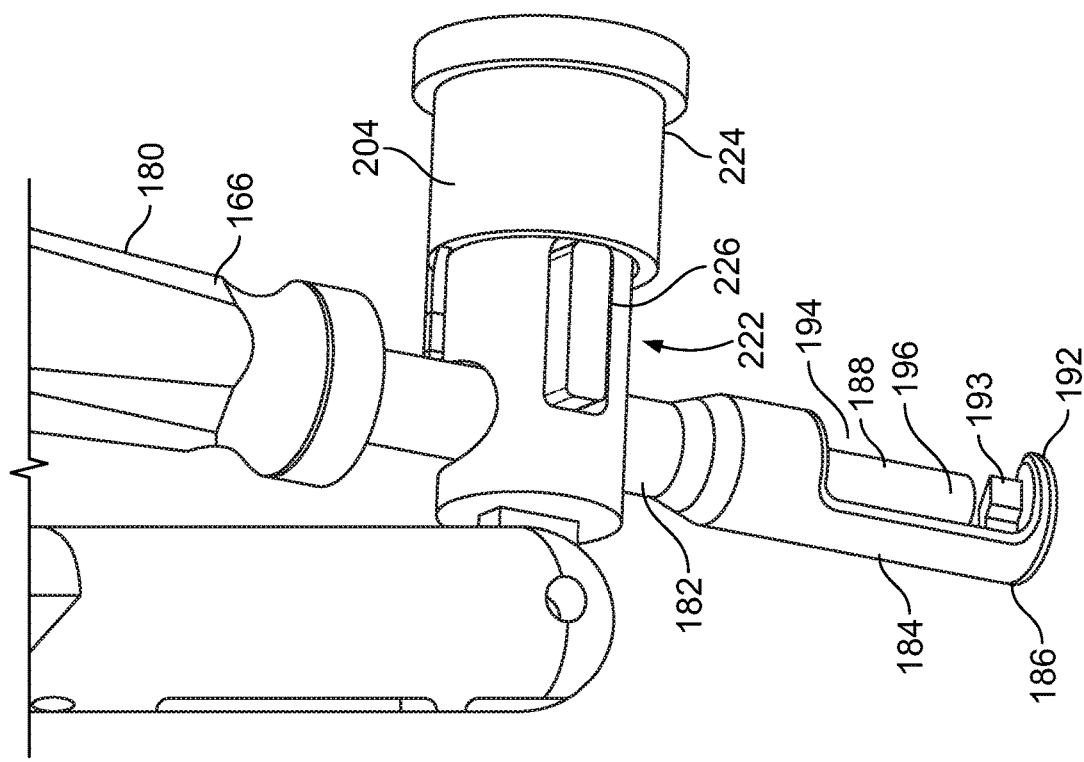

As illustrated by at least FIGS. 15A and 15B, the engagement body 184 may include a first end 190 and a second end 192 that are, at least in part, separated by a cavity 194. The cavity 194 may be sized to at least receive insertion of the clamping nut 146 as well as accommodate slidable engagement of a portion of the engagement member 188 with/from the clamping nut 146. Additionally, according to certain embodiments, the second end 192 of the engagement body 184 may include a recess 193 that is sized to matingly engage an outer portion or feature of a screw 122 in a manner that at least assists in preventing relational displacement of the screw 122 as a portion of the joystick 166 is operated to rotatably displace the clamping nut 146. Moreover, the recess 193 may engage the screw 122 in a manner that provides a counter torque to the torque the joy stick 166 may exert on the clamping nut 146. For example, according to certain embodiments, the recess 193 in the second end 192 may include one or more sides that engage a mating side(s) of an exposed portion of the screw 122, such as, for example, one or more sides of a hexagonal or square feature of the screw 122, among other features.

The engagement member 188 extends from between a distal end 196 and an opposing proximal end of the engagement member 188. At least a portion of the engagement member 188 slides along a portion of the body portion 170 of the joystick 166 as the handle 168 is displaced between the first and second positions. According to certain embodiments, the proximal end of the engagement member 188 is configured to be coupled to the connector 172 of the handle 168. Moreover, according to certain embodiments, the proximal end of the engagement member 188 may be engaged, directly or indirectly, with a portion of the shaft portion 178 of the handle 168 at least as the handle 168 is displaced to the second position. Additionally, the engagement member 188 may be coupled to the handle 168 in a manner such that the engagement member 188 is rotatably displaced with the rotational displacement of the handle 168 about the body portion 170 of the joystick 166.

As indicated by at least FIG. 8B, according to the illustrated embodiment, when the handle 168 is the first position, the engagement member 188 is in a first, retracted position in which the engagement member 188 is at least partially retracted into the tubular segment 182 and/or grip section 180 to an extent that may accommodate and/or enhance the ease with which, the clamping nut 146 may be received into the cavity 194 of the engagement body 184. According to such an embodiment, with the clamping nut 146 positioned in the cavity 194 and an exposed feature of the screw 122 matingly engaged with the recess 193 in the second end 192 of the engagement body 184, the handle 168 may be axially displaced from the first position to the second position, as shown in at least FIG. 14. With the handle 168 in the second position, at least the distal end 196 of the engagement member 188 may be operably engaged with the clamping nut 146. Accordingly, rotational displacement of the handle 168, and thus of the engagement member 188, may be translated into rotational displacement of the clamping nut 146. During such rotation of the handle 168, engagement member 188, and clamping nut 146 relative to the body portion 170 of the joystick 166, the engagement of the exposed feature of the screw 122 with the recess 193 in the second end 192 of the engagement body 184 may prevent similar rotational displacement of the screw 122. Accordingly, with the joystick 166 operably engaged with both the screw 122 and the clamping nut 146 in such a manner, the axial position of the clamping nut 146 relative to at least the screw axis of the screw 122 may be adjusted. Such adjustment in the position of the clamping nut 146 may tighten or loosed the screw clamp 142, and thus accommodate adjustment, or conversely secure, the angular position of the screw clamp 142 about the screw axis, as well as adjust the clamping force provided by the clamping bore 154. Further, such adjustment in the position of the clamping nut 146 relative to the screw axis of the screw 122 may adjust the force exerted by the screw clamp 142 on the rod clamp 144 so that the angular orientation of the rod clamp 144 relative to at least the screw clamp 142 may be adjusted or secured, as well as adjust the clamping force of the clamping orifice 164, as previously discussed.

As illustrated in FIG. 13A, a pair of joysticks 166 can be utilized to tighten and/or loosen the clamping nuts 146 about their respective screws 122. According to the illustrated embodiment, the joysticks 166 may initially tighten the clamping nuts 146 in a manner that assists in returning the clamps 138 in engagement with the respective screw 122 but which does not lock at least the angular orientation of the screw clamp 142 and/or the rod clamp 144. For example, according to certain embodiments, the joysticks 166 may be rotated one or two revolutions to keep the clamps 138 engaged with the screws 122. According to certain procedures, during tightening of the clamping nuts 146 using the joysticks 166, the operator may be observant of the level of the clamps 138 and clamping nuts 146 relative to the associated screw 122 so as to at least attempt to ensure that there will be adequate skin coverage above the clamping nut 146. However, the operator may also seek to avoid fully inserting the screw 122 down to the bone as to at least attempt to avoid the occurrence of associated femoral nerve palsy. Further, over insertion of the screw 122 into the bone may result in impingement of the lateral femoral nerve or other tissues beneath the implant rod 140.

With the clamps 138 engaged with the implanted or driven screws 122, and the joysticks 166 engaged with the screws 122 and/or clamps 138, the user may exert a force on the joysticks 166 to manipulate the bone fragments, such as, for example, fractured portions of the pelvis 104 to or around a selected position and/or orientation. Further, as shown in FIG. 13B, with the fractured portions of the bone of the pelvis 104 manipulated into position through at least the user exerting a force(s) on the joysticks 166, the user may observe indicia on the outer surface of the template rod 126 to determine a size of the implant rod 140 that is to be implanted into the patient. Selection of the size of the implant rod 140 may involve a variety of considerations, including, for example, selecting a size, such as length, that provides a degree of overhang on or past, the screw 122, such as, for example an overhang of about 5 millimeters (mm) and/or less than about 10 millimeters (mm), among other lengths. Further, at least one end of the template rod 126 may include indicia that may be used for purposes of determining the length of the implant rod 140 that is to be implanted into the patient. For example, the indicia on one or both ends of the template rod 140 that extend beyond the adjacent clamp 138 may provide an indication of the length of implant rod 140 that is to be selected for implantation.

The implant rod 140 can have, and/or be available, in a variety of shapes and sizes. For example, according to certain embodiments, the implant rod 140 can have a diameter of about 6.0 millimeters (mm) and a length of about 230 millimeters (mm) to about 350 millimeters (mm). Further, according to certain embodiments, the implant rod 140 can, at least initially, have an initial contoured radius so as to minimize the amount of adjustment of the implant rod 104 may be subsequently involved when, during implantation, matching the implant rod 140 to the patient's anatomy. The implant rod 140 can be subsequently bent or contoured to generally conform to the shape of the template rod 126. In at least certain instances, contouring or bending of the implant rod 140 may seek implement a plurality of bends or curves rather than have one or more relatively large bends or curves.

The opposing ends of the implant rod 140 can also have a configuration that facilitates relatively safe and easy implantation of the implant rod 140 into the patient. For example, according to certain embodiments, the ends of the implant rod 140 may be generally devoid of relatively sharp angled corners, and instead be rounded or include chamfers that can minimize potential harm to the patient, and which can improve the ease with which the implant rod 140 is placed across the abdomen of the patient and assembled to other components of the internal pelvic fixator 100.

With the size of the implant rod 140 selected, the template rod 126 may be removed from the clamps 138 and the patient. With the length for the implant rod 140 selected, the removed template rod 126 may be utilized in connection with the bending of the implant rod 140. Moreover, the implant rod 140 may be bent using rod benders to match the shape of the removed template rod 126. Referencing FIG. 14, the implant rod 140 may be inserted across the abdomen of the patient, beneath the tissues. The implant rod 140 may then be inserted into the rod clamp 144 of the first of the pair of clamps 138, which may or may not be positioned on or removed from the associated screw 122. In the event that the first clamp 138 was disengaged with the screw 122 when the implant rod 140 was positioned in the clamping orifice 164 of the rod clamp 144, the first clamp 138 may be connected to its associated screw 122. The joystick 166 may also be utilized to provisionally tighten the clamping nut 146 of the first clamp 138 to the screw 122.

Figure 12:
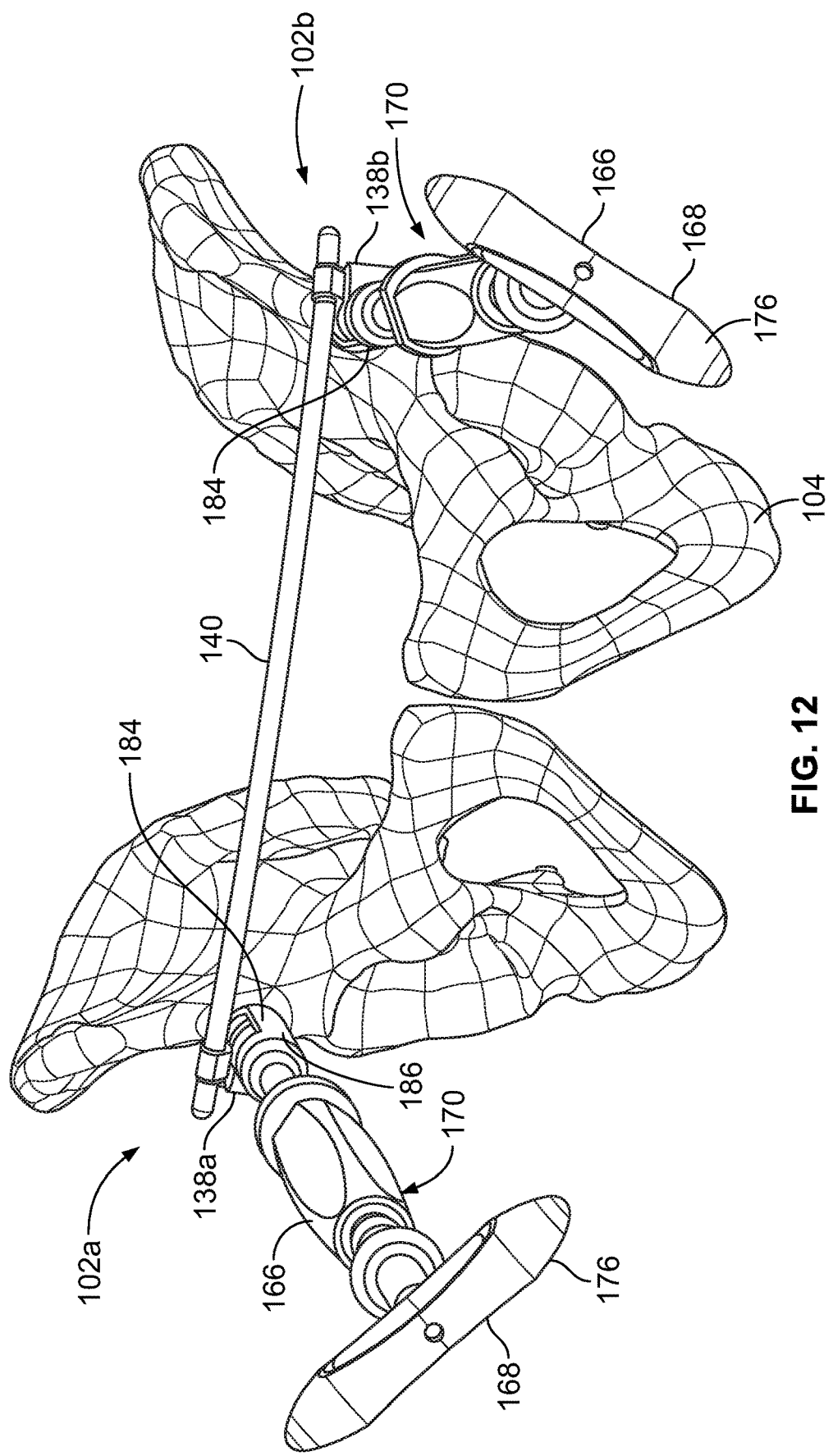
FIG. 12 illustrates a front side perspective view of a template rod being secured to first and second clamps through the operation of first and second joysticks in connection with reducing a size of a fracture in the pelvis.
Figure 14:
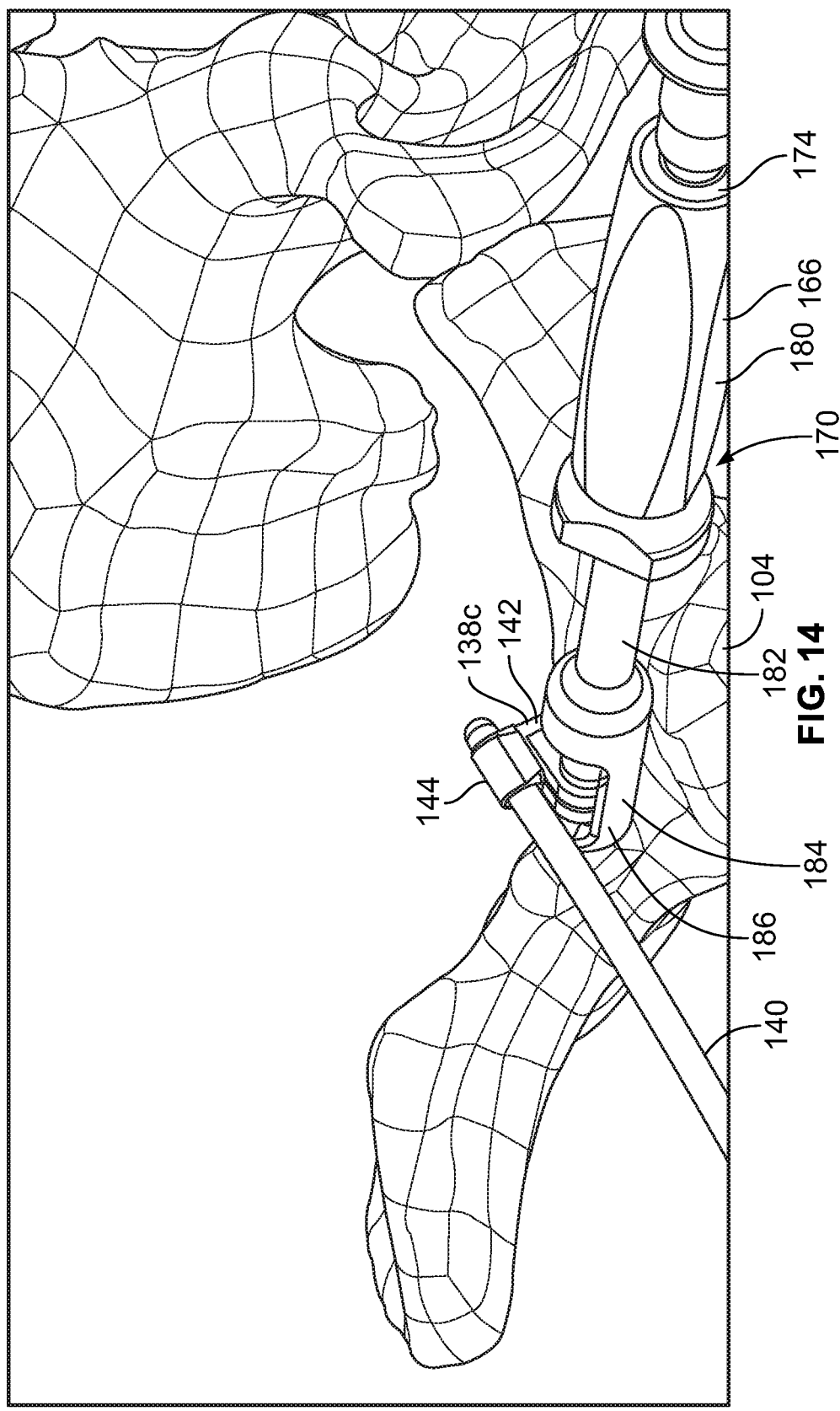
FIG. 14 is a top perspective view of a template rod being inserted into a first clamp.

Referencing FIGS. 12 and 14, with the first clamp 138 provisionally tightened to the screw 122, the implant rod 140 may be positioned in the rod clamp 144 of the first clamp 138 at a selected position. For example, according to certain embodiments, the implant rod 140 may be positioned within the rod clamp 144 of the first clamp 138 such that the implant rod 140 overhangs from the first clamp 138, as shown in FIG. 12. For example, the implant rod 140 may be positioned to overhang by 10 millimeters (mm) past the first clamp 138. Further, with both clamps 138 engaged by a respective first or second joystick 166, the user may exert on force on the joysticks 166 that reduces the fracture while aligning the implant rod 140 to the second clamp 138. Once the implant rod 140 is aligned to the second clamp 138, the user may lock the first clamp 138 to the associated screw 122, such as, for example, via rotation of the handle 168 and the associated engagement member 188 of the first joystick 166.

According to certain embodiments, after the user locks the first clamp 138 to the associated screw 122, the user may proceed with locking the second clamp 138 to the associated screw 122, such as, for example, via rotation of the handle 168 and the associated engagement member 188 of the second joystick 166. Alternatively, referencing FIGS. 15A, 15B, and 16, according to other embodiments, a reduction holder 200 may be positioned into operable engagement with the first and second joysticks 166. The reduction holder 200 may be configured to assist in providing an additional compressive force(s) that assists in maintaining a relative position of at least the first and second joysticks 166 such that the selected reduction of the fraction is maintained. Further, according to certain embodiments, the reduction holder 200 may be adjustable along one or more directions so as to either provide an increased compressive force between the first and second joysticks 166 that may further reduce the size of the fracture and/or release a degree of compression that allows for an increase in the size of the reduction. The reduction holder 200 may have a variety of different configurations. For example, according to certain embodiments, the reduction holder 200 includes a strut 202 having a pair of pivotal couplers 204 on opposing first and second ends 206, 208 of the strut 202. The couplers 204 each include a coupler body 210 having an opening 220 that is sized to receive insertion of a portion of the body portion 170 of the joystick 166, such as, for example, the tubular segment 182 of the joystick 166, as shown for example in FIGS. 15A and 15B.

The couplers 204 may include a lock mechanism 222 that may cover at least an inlet portion of the openings 220 so as to prevent the joystick 166 from being removed from the opening 220, as shown in FIG. 15B. Moreover, the lock mechanism 222 may include a sleeve 224 that is slidably adjustable over at least a portion of the coupler body 210 from the unlocked position, as shown in FIG. 15A, to a locked position, as shown in FIG. 15B. Further, the lock mechanism 222 may include a retention member 226 that may be positioned to prevent displacement of the sleeve 224 to the locked position. For example, according to certain embodiments, the retention member 226 may be biased to a position in which the retention member 226 protrudes from the coupler body 210 in a manner that prevents the sleeve 224 from being displaced to the locked position. According to such an embodiment, when the retention member 226 is depressed, the retention member 226 may be at least partially retracted into the coupler body 210 so as to no longer prevent the sleeve 224 from being displaced to the locked position. Further, according to certain embodiments, the sleeve 224 may be biased toward or to the locked positioned, such as, for example, biased by a spring.

Figure 16:
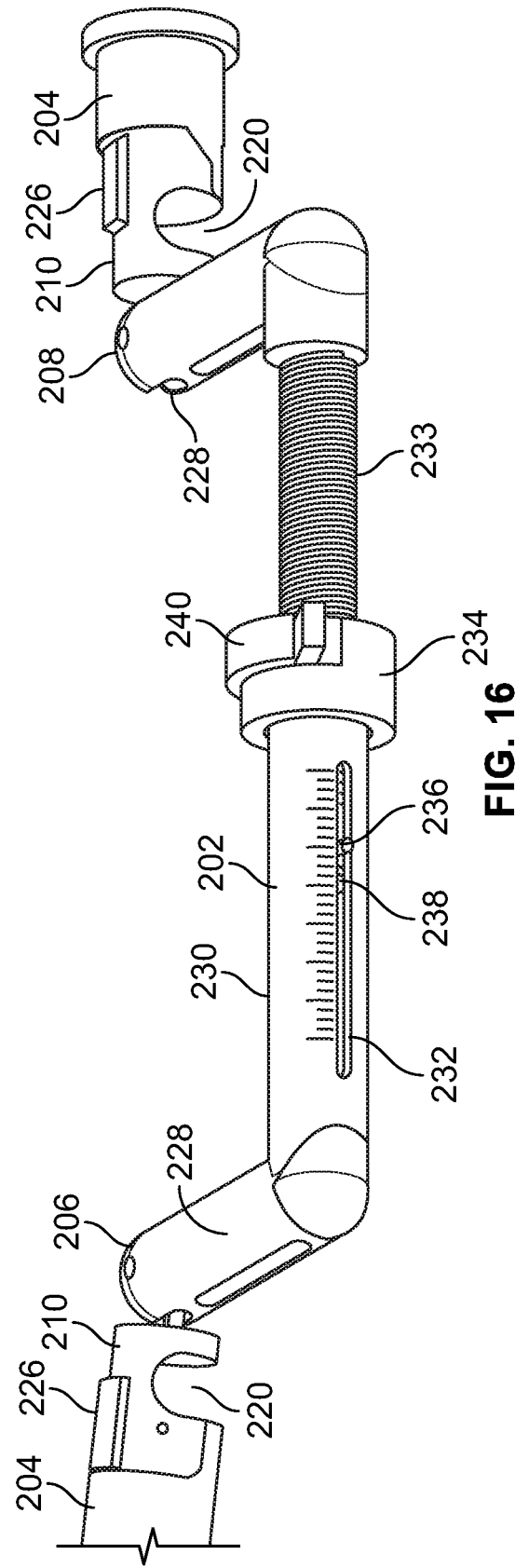
FIG. 16 illustrates a front side perspective view of a reduction holder.

The strut 202 may include a pair of arms 228 that extend from opposing ends of a strut body 230, and which are each pivotally coupled to a coupler 204. Further, according to certain embodiments, the strut body 230 may be comprised of a first member 232 and a second member 233, the first and second members 232, 233 being adjustably coupled together in a manner that accommodates adjustment in the distance between the arms 228, and thus between the couplers 204. For example, as shown in FIG. 16, the first and second members 232, 233 of the strut body 230 may be coupled together by an adjustable threaded connection. Thus, the rotational displacement of a threaded nut member 234, which can be coupled to the first member 232, about an external thread of the second member 233 may result in a linear adjustment in the distance between the arms 228, and thus between the couplers 204. Further, the extent or degree of such adjustment may be indicated by a visual indicator. For example, according to the illustrated embodiment, the second member 233 may include or be coupled to a marker 236 that is positioned within a slot 238 in the first member 232. Further, the first member 232 may, according to the depicted embodiment, include a scale that provides an indication of the relative positions, or distances therebetween, of a portion of the opposing couplers 204. Further, according to certain embodiments, a lock device 240 may be positioned to prevent adjustment in the distance between the arms 228 and the couplers 204, and thus retain the distance between the first and second joysticks 166 that are engaged with the associated screws 122 when the lock device 240 is in a locked position. Similarly, when the lock device 240 is in the unlocked position, the lock device 240 may not prevent adjustments in the distance between the arms 228 and/or between the couplers 204. Accordingly, with the lock device 240 in the unlocked position, the threaded nut member 234 may be manipulated to reduce the distance between the first and second joysticks 166 that are retained in the opening 220 of the couplers 204, and thereby further reduce the fracture. According to certain embodiments, when a selected fracture reduction is attained, and with the joysticks 166 still retained in the openings 220 of the coupler bodies 210, the handle 168 of the second joystick 166 may be rotated such that the engagement member 188 of the rotatably displaces the clamping nut 146 in a manner that tightens the second clamp 138 about the associated screw 122.

According to certain embodiments, with both clamps 138a, 138b tightened, the reduction holder 200 can be removed from engagement with the joysticks 166, as shown in FIG. 1A. Further, the joysticks 166 may be disengaged from the screws 122. The internal pelvic fixator 100, as shown for example in FIG. 1B, may then remain in the patient for a duration that may at least assist in the healing of the pelvis 104. Further, according to certain embodiments, prior to closing the incisions in the patient, debriding of the area around the implants can occur, wherein dead muscle or other tissue can be removed from the patient. Such removal may reduce the incidence of heterotopic ossification.

Figure 17A:
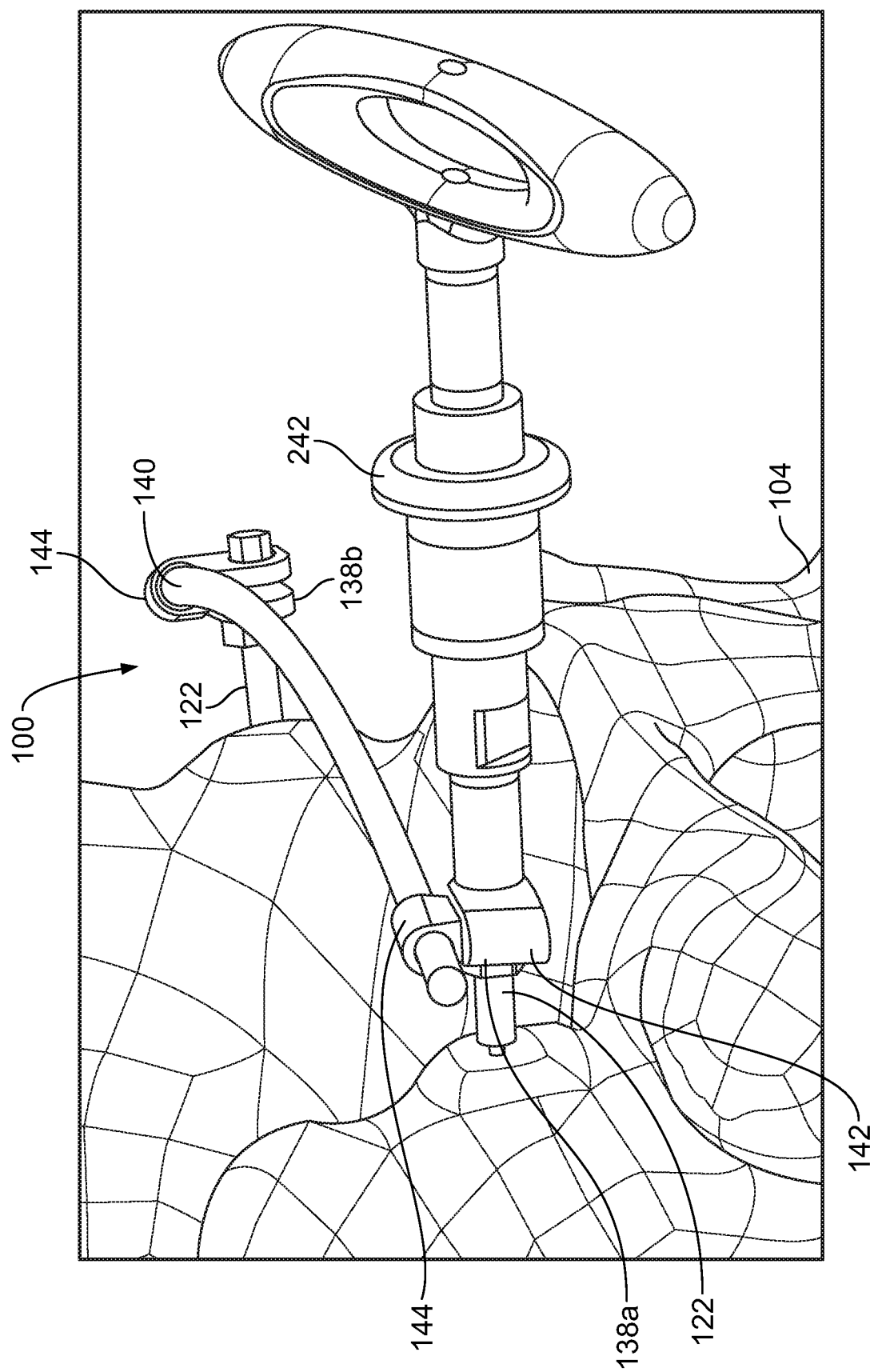
FIG. 17A illustrates a nut driver having a modified T-shaped handle loosening a clamping nut of a clamp that is engaged with an implanted screw to loosen the force of the first and second clamps on an implant rod.
Figure 17B:
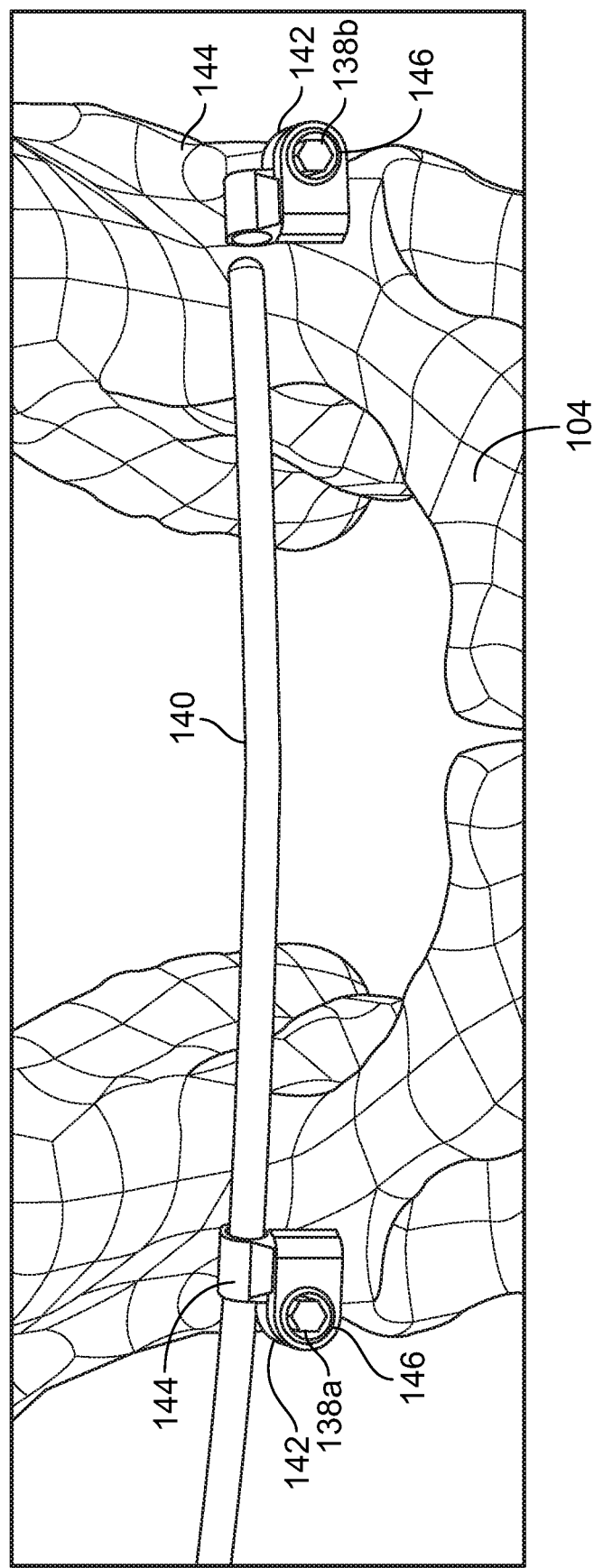
FIG. 17B illustrates a front view of an end of a bent rod removed from one of a pair of clamps.

During retrieval of the internal pelvic fixator 100, rongeurs can be used to remove heterotopic ossification (HO) that may have grown around or into the patient. Further, as shown in FIG. 17A, a nut driver 242 can engage the clamps 138a, 138b that are engaged with the screws 122 that are implanted in bone of the patient so as to at least loosen the clamping force being exerted by the clamping orifice(s) 164 on the implant rod 140. With the clamping force of the clamping orifice 164 of the rod clamp 144 removed or reduced, the implant rod 140 may be removed from engagement with the clamps 138a, 138b and from the patient, as depicted in FIG. 17B.

The implanted or driven screws 122 may be removed from the bone of the pelvis 104 with or without the clamps 138 still engaged with the screws 122. For example, FIG. 18A illustrates a drive tool 244 that is structured to facilitate removal of screws 122 from the bone while the clamps 138a, 138b are still engaged with the respective screw 122. According to such an embodiment, the drive tool 244 includes a drive portion 246 having a distal end 254 that is removably coupled to a first end 250 of an engagement section 248. A second end 252 of the engagement section 248 may include a recess that is similar to the recess 193 of the engagement body 184 of the joystick 166 that is sized to matingly engage an outer portion or feature of a screw 122 in a manner that at least assists in translating rotational displacement of the drive tool 244 to the screw 122 so as to rotate the screw in a direction that backs the screw 122 out of the bone. For example, according to certain embodiments, the recess in the second end 252 may include one or more sides that engage a mating side(s) of an exposed portion of the screw 122, such as, for example, sides of a hexagonal or square feature of the screw 122, among other features. Additionally, the engagement section 248 may include a cavity 256 that is sized to receive at least a portion of a clamp 138 and screw 122 so that the recess in the second end 252 of the engagement section 248 may be positioned to operably engage the screw 122.

The drive portion 246 may extend between a proximal end 258 and the distal end 254. The distal end 254 of the drive portion 246 may be coupled to the engagement section 248 in a number of different manners, including, for example, a snap fit or an AO connection, among other connections and/or fasteners. Additionally, the distal end 254 of the drive portion 246 and the first end 250 of the engagement section 248 may include a lock feature that assists with ensuring the engagement section 248 is rotated with the drive portion 246 from being rotated independently of the engagement section 248. For example, according to the illustrated embodiment, one of the engagement section 248 and the drive portion includes a tab 262 that extends into a recess in the other of the engagement section 248 and the drive portion 246. The proximal end 258 of the drive portion 246 may also include a handle portion 264 that is configured to be engaged by a hand of a user of the drive tool 244. For example, according to the illustrated embodiment, an end of the handle portion 264 has a T-shape that may improve the ease of engaging the handle portion 264 and/or strength of the gripping force a user may exert on the handle portion 264. According to such an embodiment, with the recess in the second end 252 of the engagement section 248 operably engaged with at least a portion of the screw 122, such as, for example, operably engaged with a portion of a hexagonal shaped feature of the screw 122, a user may exert a rotational force on the handle portion 264 that is translated to the screw 122. According to such an embodiment, the user may continue to exert rotational forces on the handle portion 264 until the working threads of the screw 122 that are implanted in the bone are backed out from the bone to a degree that allows removal of the screw 122, and attached clamp 138, from the patient.

FIG. 18B illustrates a drive tool 244' that is structured to remove a clamp 138 from the screw 122. Unlike the drive tool 244 of FIG. 18A, the drive tool 244' shown in FIG. 18B is structured to accommodate rotational displacement of the handle portion 264' about the engagement section 248'. Moreover, according to such an embodiment, the handle portion 264' includes a drive shaft 266 that extends into a portion of the engagement section 248' such that an engagement section 268 of the drive shaft 266 may be positioned in the cavity 256 of the engagement section 248' such that the engagement end 268 may operably engage the clamping nut 146. The engagement end 268 may include an aperture that is configured to engage one or more surfaces of the clamping nut 146, such as, for example, hexagonal surfaces of the clamping nut 146, in a manner that rotational displacement of the handle portion 264' is translated to the clamping nut 146. Further, according to such an embodiment, a recess in the second end 252 of the engagement section 248 may engage the screw 122 in a manner in that prevents rotation of the screw 122 while the clamping nut 146 is rotated by rotational displacement of the handle portion 264'.

Figure 19:
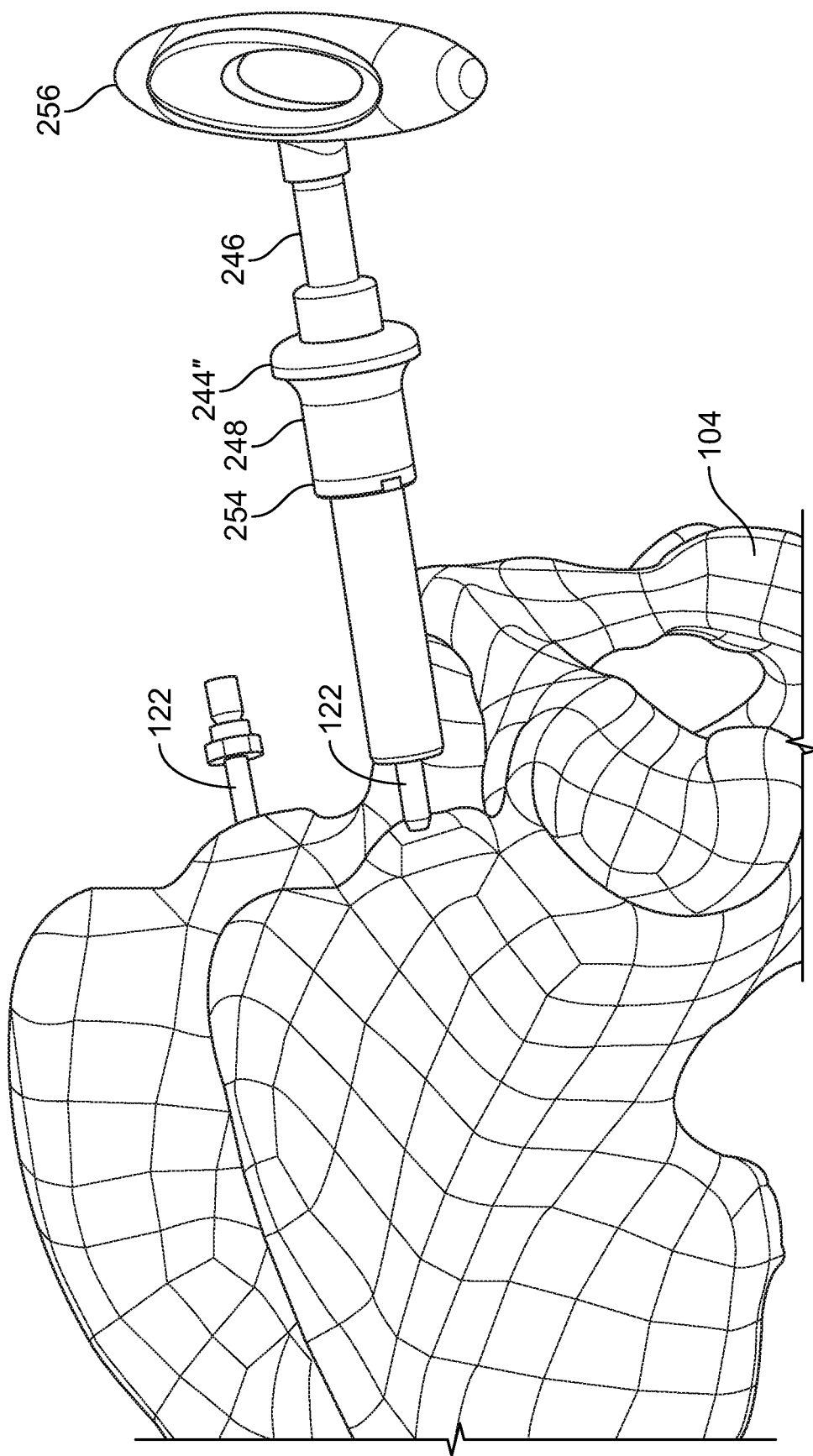
FIG. 19 illustrates a side view of a drive tool structured to remove a screw from a pelvis after a clamp has been disengaged from the screw.

FIG. 19 illustrates a side view of a drive tool 244" that is structured to remove a screw 122 from a pelvis 104 after a clamp 138 has been disengaged from the screw 122. According to such an embodiment, the handle portion 264" is coupled to a screwdriver 134. Further, while embodiments herein have been discussed with respect to handles 168 or handle portions 264, 264', 264" that may be gripped by users, according to other embodiments, such handles 168 or handle portions 264, 264', 264" may be structured to be coupled to a power tool or powered hand piece that may provide power to back the screw 122 out of the bone.

While the application has been described in connection with what is presently considered to be the most practical and preferred embodiment, it is to be understood that the application is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the application, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. An internal pelvic fixation kit, comprising:
   at least one template rod sized to extend at least between opposing sides of a pelvis bone of a patient, the at least one template rod being manually bendable during implantation to generally conform to the anatomy of the patient;
   a first clamp and a second clamp, the first and second clamps structured for selective and lockable rotation about one or more axes, the first and second clamps each having a clamping bore, the clamping bore being selectively adjustable between an uncompressed state and a compressed state;
   at least one implant rod, the clamping bore of the first and second clamps sized to receive insertion of an end of the at least one template rod and to exert a clamping force on the at least one template rod when the clamping bore is in the compressed state; and
   at least one guide sized to be positioned adjacent to a portion of the pelvis bone, the at least one guide having indicia indicative of an offset position from placement of at least one of following away from the pelvis bone: a) the first clamp, b) the second clamp, c) the at least one template rod, and d) the at least one implant rod.

2. The kit of claim 1, further comprising:
   at least one guide wire, at least a portion of the at least one guide wire structured to pass through an inner region of the at least one guide; and
   a driver structured to drive a bone screw into the pelvis bone, the driver including indicia indicative of the location of the offset position when the driver is engaged with the bone screw and the bone screw is operably engaged with the pelvis bone.

3. The kit of claim 2, wherein an outer surface of the at least one guide wire includes a plurality of indicia corresponding to a depth the at least one guide wire is inserted into the pelvis bone.

4. The kit of claim 1, further comprising a first rod offset tool and a second rod offset tool, each of the first and second rod offset tools having a channel sized to receive placement of at least a portion of the at least one template rod at opposing sides of the pelvis bone, the first and second offset tools structured to adjust the size of an offset between the at least one template rod and an adjacent outer surface of the pelvis bone.

5. The kit of claim 1, wherein at least one end of the at least one template rod includes indicia that corresponds to a length of the at least one implant rod.

6. The kit of claim 1, wherein the first clamp includes a first clamping segment and a second clamping segment, the first clamping segment structured to be rotatable about the first axis of a first bone screw when the first clamp is in an unlocked state, and be secured at an angular position relative to the first axis when the first clamp is in a locked state, the first clamping segment having a first segment bore that extends along the second axis, at least a portion of the second clamping segment extending into the first segment bore and being rotatable about the second axis, the clamping bore of the first clamp being positioned in a portion of the second clamping segment.

7. The kit of claim 1, further comprising at least one joystick, the at least one joystick having a handle, a body portion, and an engagement member, the handle extending through at least a portion of the body portion and coupled to the engagement member, the engagement member being axially displaceable by axial displacement of the handle relative to the body portion, the engagement member further being rotatable by rotation of the handle, the engagement member being configured to be removably coupled to at least one of the first and second clamps in a manner that translates rotational movement of the engagement member to a nut of the first or second clamp.

8. The kit of claim 7, wherein the at least one joystick further comprises an engagement member coupled to the body portion, the engagement member having a cavity positioned between a first end and a second end of the engagement member, at least a portion of the engagement body sized for axial and rotational displacement within the cavity, the second end of the engagement member having a recess sized to engage a screw that is coupled to one of the first and second clamps in a manner that prevents rotation of the screw as the engagement body is coupled to, and rotates, the nut of the first or second clamp.

9. The kit of claim 7, further comprising a reduction holder mechanism having a strut mechanism, a first pivotal coupler, and a second pivotal coupler, the first and second pivotal couplers pivotally connected to opposing ends of the strut mechanism, the first and second pivotal couplers each having an opening sized to receive insertion of a portion of the at least one joystick, the strut mechanism structured to adjust an axial distance between at least the first and second pivotal couplers.

10. The kit of claim 9, wherein the first and second pivotal couplers each include a lock mechanism, the lock mechanism being displaceable between a first position and a second position, the lock mechanism structured to retain the received portion of the at least one joystick when the lock mechanism is in the second position.

11. The kit of claim 9, wherein the strut mechanism includes a lock device that is adjustable between a locked state and an unlocked state, the lock device structured to prevent adjustment of an axial length of at least the strut mechanism when the lock device is in the locked state.

* * * * *